US008679763B2

(12) United States Patent
Brace et al.

(10) Patent No.: US 8,679,763 B2
(45) Date of Patent: Mar. 25, 2014

(54) EEF2K AS MODIFIERS OF THE PTEN/AKT PATHWAY AND METHODS OF USE

(75) Inventors: Arthur Brace, Redwood City, CA (US); Robert A. Blake, San Carlos, CA (US); Lori S. Friedman, San Carlos, CA (US); Lynn Margaret Bjerke, Sutton (GB); Kevin M. Ward, San Francisco, CA (US); Susana Nieto-Bergman, Berkeley, CA (US)

(73) Assignee: Exelixis, Inc., South San Francisco, CA (US)

( * ) Notice: Subject to any disclaimer, the term of this patent is extended or adjusted under 35 U.S.C. 154(b) by 1018 days.

(21) Appl. No.: 11/908,114

(22) PCT Filed: Mar. 10, 2006

(86) PCT No.: PCT/US2006/008675
§ 371 (c)(1),
(2), (4) Date: Sep. 7, 2007

(87) PCT Pub. No.: WO2006/099181
PCT Pub. Date: Sep. 21, 2006

(65) Prior Publication Data
US 2008/0193438 A1      Aug. 14, 2008

Related U.S. Application Data

(60) Provisional application No. 60/660,207, filed on Mar. 10, 2005.

(51) Int. Cl.
*G01N 33/53*   (2006.01)
*G01N 33/58*   (2006.01)
*G01N 33/15*   (2006.01)
*G01N 33/487*  (2006.01)
*G01N 33/577*  (2006.01)

(52) U.S. Cl.
USPC .............................. 435/7.1; 435/7.9; 435/7.93

(58) Field of Classification Search
None
See application file for complete search history.

(56) References Cited

FOREIGN PATENT DOCUMENTS

| WO | WO 02/079779   | * | 10/2002 | ............. G01N 33/50 |
| WO | WO 2005/001026 | * | 1/2005  |                          |
| WO | WO 2005/010148 | * | 2/2005  |                          |

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Phillips, A., J Pharm Pharmacology 53: 1169-1174, 2001.*
Vidal et al. European Journal of Cancer. 41: 2812-2818, 2005.*
Pirollo et al. Cancer Res. 68(5): 1247-1250, 2008.*
Tannock and Hill. The Basic Science of Oncology. 1998. New York: McGraw-Hill.*
Song et al., Expert Opin Biol Ther 7(4): 431-438, 2007.*
Website from genecards.org/cgi-bin/carddisp.pl?gene=Eef2k (hereafter GeneCards Website, downloaded Feb. 8, 2011; 8 pages total.*
Wang et al., Nuc. Acids Res. 27: 4609-4618, 1999.*
Kaufman et al., Blood 94: 3178-3184, 1999.*
Demian et al., Journal of Biomolecular Screening, 2009; 14: 838-844.*
Anita Chan et al.: "Activation of AMP-activated Protein Kinase Inhibits Protein Synthesis Associated With Hypertrophy in the Cardiac Myocyte," The Journal of Biological Chemistry, Jul. 2004, vol. 279, No. 31, pp. 32771-32779.
Sandrine Horman et al.: "Myocardial Ischemia and Increased heart Work Modulate the Phosphorylatino State of Eukaryotic Factor-2," The Journal of Biological Chemistry, Oct. 2003, vol. 278, No. 43, pp. 41970-41976.
Xumin Wang et al.: "Regulation of elongation factor 2 kinases by p90RSK1 and p70 S6 kinase," 2001; EMBO Journal, vol. 20, No. 16, pp. 4370-4379.
Sonia Arora et al.: "Detection of anti-elongation factor 2 kinase (calmodulin-dependent protein kinase III) antibodies in patients with systemic lupus erythrematosus," biochemical and Biophysical Research Communications (BBRC); 2002; vol. 298, pp. 1073-1076.
T.J. Parmer et al.: "Activity and regulation by growth factors of calmodulin dependent protein kinase III (elongation factor 2-kinase) in human breast cancer," British journal of Cancer (BJC); 1999, vol. 79, No. 1, pp. 59-64.
Genbank Reference No. 33469142, entitled: "*Homo sapiens* leucine-rich repeat kinase 1 (LRRK1), mRNA," dated Aug. 21, 2004.
Genbank Reference No. NM_001702, entitled: "*Homo sapiens* brain-specific angiogenesis inhibitor 1 (BAI1), mRNA," dated Aug. 23, 2004.
Genbank Reference No. NM_003505, entitled: "*Homo sapiens* frizzled family receptor 1 (FZD1), mRNA," dated Mar. 2, 2005.
Genbank Reference No. NM_004367, entitled: "*Homo sapiens* chemokine (C—C motif) receptor 6 (CCR6), transcript variant 1, mRNA," dated Mar. 2, 2005.

(Continued)

*Primary Examiner* — Bridget E Bunner
*Assistant Examiner* — Christina Borgeest
(74) *Attorney, Agent, or Firm* — McDonnell Boehnen Hulbert & Berghoff LLP

(57) ABSTRACT

Human EEF2K genes are identified as modulators of the PTEN/AKT pathway and thus are therapeutic targets for disorders associated with defective PTEN/AKT function. Methods for identifying modulators of PTEN/AKT comprising screening for agents that modulate the activity of EEF2K are provided.

7 Claims, No Drawings

(56) References Cited

OTHER PUBLICATIONS

Genbank Reference No. NM_031409, entitled: "*Homo sapiens* chemokine (C—C motif) receptor 6 (CCR6), transcript variant 2, mRNA," dated Mar. 2, 2005.
Genbank Reference No. NM_000020, entitled: "*Homo sapiens* activin A receptor type II-like 1 (ACVRL1), mRNA," dated Oct. 26, 2004.
Genbank Reference No. NM_178170, entitled: "*Homo sapiens* NIMA (never in mitosis gene a)—related kinase 8 (NEK8), mRNA," dated Oct. 27, 2004.
Genbank Reference No. NM_025233, entitled: "*Homo sapiens* CoA synthase (COASY), nuclear gene encoding mitochondrial protein, transcript variant 1, mRNA," dated Mar. 2, 2005.
Genbank Reference No. NM_022445, entitled: "*Homo sapiens* thiamin pyrophosphokinase 1 (TPK1), transcript variant 1, mRNA," dated Mar. 2, 2005.
Genbank Reference No. NM_018654, entitled: "*Homo sapiens* G protein-coupled receptor, family C, group 5, member D (GPRC5D), mRNA," dated Mar. 2, 2005.
Genbank Reference No. NM_080836, entitled: "*Homo sapiens* serine/threonine kinase 35 (STK35), mRNA," dated Mar. 2, 2005.
Genbank Reference No. NM_002860, entitled: "*Homo sapiens* aldehyde dehydrogenase 18 family, member A1 (ALDH18A1), nuclear gene encoding mitochondrial protein, transcript variant 1, mRNA," dated Mar. 2, 2005.
Genbank Reference No. NM_013447, entitled: "*Homo sapiens* egf-like module containing, mucin-like, hormone receptor-like 2 (EMR2), transcript variant 1, mRNA," Oct. 26, 2004.
Genbank Reference No. NM_152916, entitled: "*Homo sapiens* egf-like module containing, mucin-like, hormone receptor-like 2 (EMR2), transcript variant 2, mRNA," dated Oct. 27, 2004.
Genbank Reference No. NM_152917, entitled: "*Homo sapiens* egf-like module containing, mucin-like, hormone receptor-like 2 (EMR2), transcript variant 3, mRNA," dated Oct. 27, 2004.
Genbank Reference No. NM_152918, entitled: "*Homo sapiens* egf-like module containing, mucin-like, hormone receptor-like 2 (EMR2), transcript variant 4, mRNA," dated Oct. 27, 2004.
Genbank Reference No. NM_152919, entitled: "*Homo sapiens* egf-like module containing, mucin-like, hormone receptor-like 2 (EMR2), transcript variant 5, mRNA," dated Oct. 27, 2004.
Genbank Reference No. NM_152920, entitled: "*Homo sapiens* egf-like module containing, mucin-like, hormone receptor-like 2 (EMR2), transcript variant 6, mRNA," dated Oct. 27, 2004.
Genbank Reference No. NM_152921, entitled: "*Homo sapiens* egf-like module containing, mucin-like, hormone receptor-like 2 (EMR2), transcript variant 7, mRNA," dated Oct. 27, 2004.
Genbank Reference No. XM_055866, entitled: "*Homo sapiens* lemur tyrosine kinase 3 (LMTK3), mRNA," dated Aug. 20, 2004.
Genbank Reference No. NM_001005353, entitled: "*Homo sapiens* adenylate kinase 3-like 1 (AK3L1), nuclear gene encoding mitochondrial protein, transcript variant 5, mRNA," dated Oct. 28, 2004.
Genbank Reference No. NM_013410, entitled: "*Homo sapiens* adenylate kinase 4 (AK4), nuclear gene encoding mitochondrial protein, transcript variant 6, mRNA," dated Mar. 2, 2005.
Genbank Reference No. NM_203464, entitled: "*Homo sapiens* adenylate kinase 4 (AK4), nuclear gene encoding mitochondrial protein, transcript variant 7, mRNA," dated Oct. 28, 2004.
Genbank Reference No. NM_004445, entitled: "*Homo sapiens* EPH receptor B6 (EPHB6), mRNA," dated Mar. 3, 2005.
Genbank Reference No. NM_012119, entitled: "*Homo sapiens* cyclin-dependent kinase 20 (CDK20), transcript variant 2, mRNA," dated Mar. 2, 2005.
Genbank Reference No. NM_178432, entitled: "*Homo sapiens* cyclin-dependent kinase 20 (CDK20), transcript variant 1, mRNA," dated Mar. 2, 2005.
Genbank Reference No. NM_013302, entitled: "*Homo sapiens* eukaryotic elongation factor-2 kinase (EEF2K), mRNA," dated Mar. 2, 2005.
Genbank Reference No. NM_004226, entitled: "*Homo sapiens* serine/threonine kinase 17b (STK17B), mRNA," dated Mar. 2, 2005.
Genbank Reference No. NM_018423, entitled: "*Homo sapiens* serine/threonine/tyrosine kinase 1 (STYK1), mRNA," dated Mar. 2, 2005.
Genbank Reference No. NM_019839, entitled: "*Homo sapiens* leukotriene B4 receptor 2 (LTB4R2), transcript variant 1, mRNA," dated Mar. 2, 2005.
Genbank Reference No. NM_005400, entitled: "*Homo sapiens* protein kinase C, epsilon (PRKCE), mRNA," dated Mar. 2, 2005.
Genbank Reference No. NM_006641, entitled: "*Homo sapiens* chemokine (C—C motif) receptor 9 (CCR9), transcript variant B, mRNA," dated Mar. 2, 2005.
Genbank Reference No. NM_031200, entitled: "*Homo sapiens* chemokine (C—C motif) receptor 9 (CCR9), transcript variant A, mRNA," dated Mar. 2, 2005.
Genbank Reference No. NM_032430, entitled: "*Homo sapiens* BR serine/threonine kinase 1 (BRSK1), mRNA," dated Mar. 2, 2005.
Genbank Reference No. NM_007254, entitled: "*Homo sapiens* polynucleotide kinase 3'-phosphatase (PNKP), mRNA," dated Mar. 2, 2005.
Genbank Reference No. NM_005876, entitled: "*Homo sapiens* SPEG complex locus (SPEG), transcript variant 1, mRNA," dated Oct. 27, 2004.
Genbank Reference No. XM_051005, entitled: "*Homo sapiens* KIAA1297 protein (KIAA1297), mRNA," dated Jan. 23, 2004.
Genbank Reference No. NM_001716, entitled: "*Homo sapiens* chemokine (C—X—C motif) receptor 5 (CXCR5), transcript variant 1, mRNA," dated Mar. 2, 2005.
Genbank Reference No. NM_032966, entitled: "*Homo sapiens* chemokine (C—X—C motif) receptor 5 (CXCR5), transcript variant 2, mRNA," dated Oct. 27, 2004.
Genbank Reference No. NM_153809, entitled: "*Homo sapiens* TAF1 RNA polymerase II, TATA box binding protein (TBP)-associated factor, 210kDa-like (TAF1L), mRNA," dated Oct. 27, 2004.
Genbank Reference No. NM_022755, entitled: "*Homo sapiens* inositol 1,3,4,5,6-pentakisphosphate 2-kinase (IPPK), mRNA," dated Mar. 2, 2005.
Genbank Reference No. NM_020168, entitled: "*Homo sapiens* p21 protein (Cdc42/Rac)-activated kinase 6 (PAK6), transcript variant 1, mRNA," dated Mar. 2, 2005.

\* cited by examiner

SEQUENCE LISTING

<160> NUMBER OF SEQ ID NOS: 9

<210> SEQ ID NO 1
<211> LENGTH: 725
<212> TYPE: PRT
<213> ORGANISM: Homo sapiens

<400> SEQUENCE: 1

```
Met Ala Asp Glu Asp Leu Ile Phe Arg Leu Glu Gly Val Asp Gly Gly
1               5                   10                  15

Gln Ser Pro Arg Ala Gly His Asp Gly Asp Ser Asp Gly Asp Ser Asp
            20                  25                  30

Asp Glu Glu Gly Tyr Phe Ile Cys Pro Ile Thr Asp Asp Pro Ser Ser
        35                  40                  45

Asn Gln Asn Val Asn Ser Lys Val Asn Lys Tyr Tyr Ser Asn Leu Thr
    50                  55                  60

Lys Ser Glu Arg Tyr Ser Ser Ser Gly Ser Pro Ala Asn Ser Phe His
65                  70                  75                  80

Phe Lys Glu Ala Trp Lys His Ala Ile Gln Lys Ala Lys His Met Pro
                85                  90                  95

Asp Pro Trp Ala Glu Phe His Leu Glu Asp Ile Ala Thr Glu Arg Ala
            100                 105                 110

Thr Arg His Arg Tyr Asn Ala Val Thr Gly Glu Trp Leu Asp Asp Glu
        115                 120                 125

Val Leu Ile Lys Met Ala Ser Gln Pro Phe Gly Arg Gly Ala Met Arg
    130                 135                 140

Glu Cys Phe Arg Thr Lys Lys Leu Ser Asn Phe Leu His Ala Gln Gln
145                 150                 155                 160

Trp Lys Gly Ala Ser Asn Tyr Val Ala Lys Arg Tyr Ile Glu Pro Val
                165                 170                 175

Asp Arg Asp Val Tyr Phe Glu Asp Val Arg Leu Gln Met Glu Ala Lys
            180                 185                 190

Leu Trp Gly Glu Glu Tyr Asn Arg His Lys Pro Pro Lys Gln Val Asp
        195                 200                 205

Ile Met Gln Met Cys Ile Ile Glu Leu Lys Asp Arg Pro Gly Lys Pro
    210                 215                 220

Leu Phe His Leu Glu His Tyr Ile Glu Gly Lys Tyr Ile Lys Tyr Asn
225                 230                 235                 240

Ser Asn Ser Gly Phe Val Arg Asp Asp Asn Ile Arg Leu Thr Pro Gln
                245                 250                 255

Ala Phe Ser His Phe Thr Phe Glu Arg Ser Gly His Gln Leu Ile Val
            260                 265                 270

Val Asp Ile Gln Gly Val Gly Asp Leu Tyr Thr Asp Pro Gln Ile His
        275                 280                 285

Thr Glu Thr Gly Thr Asp Phe Gly Asp Gly Asn Leu Gly Val Arg Gly
    290                 295                 300

Met Ala Leu Phe Phe Tyr Ser His Ala Cys Asn Arg Ile Cys Glu Ser
305                 310                 315                 320

Met Gly Leu Ala Pro Phe Asp Leu Ser Pro Arg Glu Arg Asp Ala Val
                325                 330                 335

Asn Gln Asn Thr Lys Leu Leu Gln Ser Ala Lys Thr Ile Leu Arg Gly
            340                 345                 350

Thr Glu Glu Lys Cys Gly Ser Pro Arg Val Arg Thr Leu Ser Gly Ser
        355                 360                 365
```

```
Arg Pro Pro Leu Leu Arg Pro Leu Ser Glu Asn Ser Gly Asp Glu Asn
    370                 375                 380

Met Ser Asp Val Thr Phe Asp Ser Leu Pro Ser Ser Pro Ser Ser Ala
385                 390                 395                 400

Thr Pro His Ser Gln Lys Leu Asp His Leu His Trp Pro Val Phe Ser
                405                 410                 415

Asp Leu Asp Asn Met Ala Ser Arg Asp His Asp His Leu Asp Asn His
            420                 425                 430

Arg Glu Ser Glu Asn Ser Gly Asp Ser Gly Tyr Pro Ser Glu Lys Arg
        435                 440                 445

Gly Glu Leu Asp Asp Pro Glu Pro Arg Glu His Gly His Ser Tyr Ser
    450                 455                 460

Asn Arg Lys Tyr Glu Ser Asp Glu Asp Ser Leu Gly Ser Ser Gly Arg
465                 470                 475                 480

Val Cys Val Glu Lys Trp Asn Leu Leu Asn Ser Ser Arg Leu His Leu
                485                 490                 495

Pro Arg Ala Ser Ala Val Ala Leu Glu Val Gln Arg Leu Asn Ala Leu
            500                 505                 510

Asp Leu Glu Lys Lys Ile Gly Lys Ser Ile Leu Gly Lys Val His Leu
        515                 520                 525

Ala Met Val Arg Tyr His Glu Gly Gly Arg Phe Cys Glu Lys Gly Glu
    530                 535                 540

Glu Trp Asp Gln Glu Ser Ala Val Phe His Leu Glu His Ala Ala Asn
545                 550                 555                 560

Leu Gly Glu Leu Glu Ala Ile Val Gly Leu Gly Leu Met Tyr Ser Gln
                565                 570                 575

Leu Pro His His Ile Leu Ala Asp Val Ser Leu Lys Glu Thr Glu Glu
            580                 585                 590

Asn Lys Thr Lys Gly Phe Asp Tyr Leu Leu Lys Ala Ala Glu Ala Gly
        595                 600                 605

Asp Arg Gln Ser Met Ile Leu Val Ala Arg Ala Phe Asp Ser Gly Gln
    610                 615                 620

Asn Leu Ser Pro Asp Arg Cys Gln Asp Trp Leu Glu Ala Leu His Trp
625                 630                 635                 640

Tyr Asn Thr Ala Leu Glu Met Thr Asp Cys Asp Glu Gly Gly Glu Tyr
                645                 650                 655

Asp Gly Met Gln Asp Glu Pro Arg Tyr Met Met Leu Ala Arg Glu Ala
            660                 665                 670

Glu Met Leu Phe Thr Gly Gly Tyr Gly Leu Glu Lys Asp Pro Gln Arg
        675                 680                 685

Ser Gly Asp Leu Tyr Thr Gln Ala Ala Glu Ala Met Glu Ala Met
    690                 695                 700

Lys Gly Arg Leu Ala Asn Gln Tyr Tyr Gln Lys Ala Glu Glu Ala Trp
705                 710                 715                 720

Ala Gln Met Glu Glu
                725

<210> SEQ ID NO 2
<211> LENGTH: 2178
<212> TYPE: DNA
<213> ORGANISM: Homo sapiens

<400> SEQUENCE: 2
atggcagacg aagacctcat cttccgcctg gaaggtgttg atggcggcca gtcccccga        60
```

```
gctggccatg atggtgattc tgatggggac agcgacgatg aggaaggtta cttcatctgc    120
cccatcacgg atgacccaag ctcgaaccag aatgtcaatt ccaaggttaa taagtactac    180
agcaacctaa caaaaagtga gcggtatagc tccagcgggt ccccggcaaa ctccttccac    240
ttcaaggaag cctggaagca cgcaatccag aaggccaagc acatgcccga ccctgggct     300
gagttccacc tggaagatat tgccaccgaa cgtgctactc gacacaggta caacgccgtc    360
accggggaat ggctggatga tgaagttctg atcaagatgg catctcagcc cttcggccga    420
ggagcaatga gggagtgctt ccggacgaag aagctctcca acttcttgca tgcccagcag    480
tggaagggcg cctccaacta cgtggcgaag cgctacatcg agcccgtaga ccgggatgtg    540
tactttgagg acgtgcgtct acagatggag gccaagctct gggggagga gtataatcgg     600
cacaagcccc ccaagcaggt ggacatcatg cagatgtgca tcatcgagct gaaggacaga    660
ccgggcaagc ccctcttcca cctggagcac tacatcgagg gcaagtacat caagtacaac    720
tccaactctg gctttgtccg tgatgacaac atccgactga cgccgcaggc cttcagccac    780
ttcactttg agcgttccgg ccatcagctg atagtggtgg acatccaggg agttggggat     840
ctctacactg acccacagat ccacgcggag acgggcactg actttggaga cggcaaccta    900
ggtgtccgcg ggatggcgct cttcttctac tctcatgcct gcaaccggat ttgcgagagc    960
atgggccttg ctccctttga cctctcgccc cgggagaggg atgcagtgaa tcagaacacc   1020
aagctgctgc aatcagccaa gaccatcttg agaggaacag aggaaaaatg tgggagcccc   1080
cgagtaagga ccctctctgg gagccggcca cccctgctcc gtccccttc agagaactct    1140
ggagacgaga acatgagcga cgtgaccttc gactctctcc cttcttcccc atcttcggcc   1200
acaccacaca gccagaagct agaccaccctc cattggccag tgttcagtga cctcgataac   1260
atggcatcca gagaccatga tcatctagac aaccaccggg agtctgagaa tagtggggac   1320
agcggatacc ccagtgagaa gcggggtgag ctggatgacc ctgagccccg agaacatggc   1380
cactcataca gtaatcggaa gtacgagtct gacgaagaca gcctgggcag ctctggacgg   1440
gtatgtgtag agaagtggaa tctcctcaac tcctcccgcc tccacctgcc gagggcttcg   1500
gccgtggccc tggaagtgca aaggcttaat gctctgacct cgaaaagaa atcgggaag    1560
tccattttgg ggaaggtcca tctggccatg gtgcgctacc acgagggtgg gcgcttctgc   1620
gagaagggcg aggagtggga ccaggagtcg gctgtcttcc acctggagca cgcagccaac   1680
ctgggcgagc tggaggccat cgtgggcctg ggactcatgt actcgcagtt gcctcatcac   1740
atcctagccg atgtctctct gaaggagaca gaagagaaca aaaccaaagg atttgattac   1800
ttactaaagg ccgctgaagc tggcgacagg cagtccatga tcctagtggc gcgagctttt   1860
gactctggcc agaacctcag cccggacagg tgccaagact ggctagaggc cctgcactgg   1920
tacaacactg ccctggagat gacggactgt gatgagggcg gtgagtacga cggaatgcag   1980
gacgagcccc ggtacatgat gctggccagg gaggcagaga tgctgttcac aggaggctac   2040
gggctggaga aggacccgca gagatcaggg gacttgtata cccaggcagc agaggcagcg   2100
atggaagcca tgaagggccg actggccaac cagtactacc aaaaggctga gaggcctgg    2160
gcccagatgg aggaataa                                                 2178
```

<210> SEQ ID NO 3
<211> LENGTH: 2178
<212> TYPE: DNA
<213> ORGANISM: Homo sapiens

<400> SEQUENCE: 3

```
atggcagacg aagatctcat cttccgcctg gaaggcgttg atggcggcca gtcccccga      60
gctggccatg atggtgattc tgatggggac agcgacgatg aggaaggtta cttcatctgc     120
cccatcacgg atgacccaag ctcgaaccag aatgtcaatt ccaaggttaa taagtactac     180
agcaacctaa caaaaagtga gcggtatagc tccagcgggt ccccggcaaa ctccttccac     240
ttcaaggaag cctggaagca cgcaatccag aaggccaagc acatgcccga cccctgggct     300
gagttccacc tggaagatat tgccaccgaa cgtgctactc gacacaggta caacgccgtc     360
accggggaat ggctggatga tgaagttctg atcaagatgg catctcagcc cttcggccga     420
ggagcaatga gggagtgctt ccggacgaag aagctctcca acttcttgca tgcccagcag     480
tggaagggcg cctccaacta cgtggcgaag cgctacatcg agcccgtaga ccgggatgtg     540
tactttgagg acgtgcgtct acagatggag gccaagctct ggggggagga gtataatcgg     600
cacaagcccc ccaagcaggt ggacatcatg cagatgtgca tcatcgagct gaaggacaga     660
ccgggcaagc ccctcttcca cctggagcac tacatcgagg gcaagtacat caagtacaac     720
tccaactctg gctttgtccg cgatgacaac atccgcctga cgccgcaggc cttcagccac     780
ttcacttttg agcgttccgg ccatcagctg atagtggtgg acatccaggg agttggggat     840
ctctacactg acccacagat ccacacggag acgggcactg actttggaga cggcaaccta     900
ggtgtccgcg ggatggcgct cttcttctac tctcatgcct gcaaccggat ttgcgagagc     960
atgggccttg ctcccttga cctctcgccc cgggagaggg atgcagtgaa tcagaacacc    1020
aagctgctgc aatcagccaa gaccatcttg agaggaacag aggaaaaatg tgggagcccc    1080
caagtaagga ccctctctgg gagccggcca cccctgctcc gtccccttc agagaactct    1140
ggagacgaga acatgagcga cgtgaccttc gactctctcc cttcttcccc atcttcggcc    1200
acaccacaca gccagaagct agaccactc cattggccag tgttcagtga cctcgataac    1260
atggcatcca gagaccatga tcatctagac aaccaccggg agtctgagaa tagtggggac    1320
agcggatacc ccagtgagaa gcggggtgag ctggatgacc ctgagcccg agaacatggc    1380
cactcataca gtaatcggaa gtacgagtct gacgaagaca gcctgggcag ctctggacgg    1440
gtatgtgtag agaagtggaa tctcctcaac tcctcccgcc tccacctgcc gagggcttcg    1500
gccgtggccc tggaagtgca aaggcttaat gctctggacc tcgaaaagaa aatcgggaag    1560
tccatttgg gaaggtcca tctggccatg gtgcgctacc acgagggtgg gcgcttctgc    1620
gagaagggcg aggagtggga ccaggagtcg gctgtcttcc acctggagca cgcagccaac    1680
ctgggcgagc tggaggccat cgtgggcctg ggactcatgt actcgcagtt gcctcatcac    1740
atcctagccg atgtctctct gaaggagaca gaagagaaca aaaccaaagg atttgattac    1800
ttactaaagg ccgctgaagc tggcgacagg cagtccatga tcctagtggc gcgagctttt    1860
gactctggcc agaacctcag cccggacagg tgccaagact ggctagaggc cctgcactgg    1920
tacaacactg ccctggagat gacggactgt gatgagggcg gtgagtacga cggaatgcag    1980
gacgagcccc ggtacatgat gctggccagg gaggccgaga tgctgttcac aggaggctac    2040
gggctggaga aggacccgca gagatcaggg gacttgtata cccaggcagc agaggcagcg    2100
atggaagcca tgaagggccg actggccaac cagtactacc aaaaggctga agaggcctgg    2160
gcccagatgg aggagtaa                                                  2178
```

<210> SEQ ID NO 4
<211> LENGTH: 3610
<212> TYPE: DNA
<213> ORGANISM: Homo sapiens -continued

```
<400> SEQUENCE: 4
ccacgcgtcc gggcccctgc gcccttcctg ggatcactcc gactgccccg cgcctctgcc      60
aactcctctg gaccctcgcg gccgtgggca gcggctgccg cgcctgtctg cccgagggag     120
gaccttcgcc tctgcatttg tccagtaact ctggctgtgc cggatactgc ttgggtaaaa     180
cgggcacccc aggaacatgg cagacgaaga tctcatcttc cgcctggaag gcgttgatgg     240
cggccagtcc ccccgagctg gccgtgatgg tgattctgat ggggacagcg acgatgagga     300
aggttacttc atctgcccca tcacggatga cccaagctcg aaccagaatg tcaattccaa     360
ggttaataag tactacagca acctaacaaa aagtgagcgg tatagctcca gcgggtcccc     420
ggcaaactcc ttccacttca aggaagcctg gaagcacgca atccagaagg ccaagcacat     480
gcccgacccc tgggctgagt tccacctgga agatattgcc accgaacgtg ctactcgaca     540
caggtacaac gccgtcaccg gggaatggct ggatgatgaa gttctgatca agatggcatc     600
tcagcccttc ggccgaggag caatgaggga gtgcttccgg acgaagaagc tctccaactt     660
cttgcatgcc cagcagtgga agggagcctc caactacgtg gcgaagcgct acatcgagcc     720
cgtagaccgg gatgtgtact ttgaggacgt gcgtctacag atggaggcca agctctgggg     780
ggaggagtat aatcggcaca agccccccaa gcaggtggac atcatgcaga tgtgcatcat     840
cgagctgaag gacagaccgg gcaagcccct cttccacctg gagcactaca tcgagggcaa     900
gtacatcaag tacaactcca actctggctt tgtccgcgat gacaacatcc gcctgacgcc     960
gcaggccttc agccacttca cttttgagcg ttccggccat cagctgatag tggtggacat    1020
ccagggagtt ggggatctct acactgaccc acagatccac acggagacgg gcactgactt    1080
tggagacggc aacctaggtg tccgcgggat ggcgctcttc ttctactctc atgcctgcaa    1140
ccggatttgc gagagcatgg gccttgctcc ctttgacctc tcgccccggg agagggatgc    1200
agtgaatcag aacaccaagc tgctgcaatc agccaagacc atcttgagag aacagagga    1260
aaaatgtggg agccccgag taaggaccct ctctgggagc cggccacccc tgctccgtcc    1320
cctttcagag aactctggag acgagaacat gagcgacgtg accttcgact ctctcccttc    1380
ttccccatct tcgccacaca cacacagcca gaagctagac cacctccatt ggccagtgtt    1440
cagtgacctc gataacatgg catccagaga ccatgatcat ctagacaacc accgggagtc    1500
tgagaatagt ggggacagcg gataccccag tgagaagcgg ggtgagctgg atgaccctga    1560
gccccgagaa catggccact catacagtaa tcggaagtac gagtctgacg aagacagcct    1620
gggcagctct ggacgggtat gtgtagaaa gtggaatctc ctcaactcct cccgcctcca    1680
cctgccgagg gcttcggccg tggccctgga agtgcaaagg cttaatgctc tggacctcga    1740
aaagaaaatc gggaagtcca tttggggaa ggtccatctg gccatggtgc gctaccacga    1800
gggtgggcgc ttctgcgaga agggcgagga gtgggaccag gagtcggctg tcttccacct    1860
ggagcacgca gccaacctgg gcgagctgga ggccatcgtg ggcctgggac tcatgtactc    1920
gcagttgcct catcacatcc tagccgatgt ctctctgaag gagacagaag agaacaaaac    1980
caaaggattt gattacttac taaaggccgc tgaagctggc gacaggcagt ccatgatcct    2040
agtggcgcga gcttttgact ctggccagaa cctcagcccg gacaggtgcc aagactggct    2100
agaggccctg cactggtaca acactgccct ggagatgacg gactgtgatg agggcggtga    2160
gtacgacgga atgcaggacg agccccggta catgatgctg gcagggagg ccgagatgct    2220
gttcacagga ggctacgggc tggagaagga cccgcagaga tcaggggact tgtataccca    2280
ggcagcagag gcagcgatgg aagccatgaa gggccgactg gccaaccagt actaccaaaa    2340
```

-continued

```
ggctgaagag gcctgggccc agatggagga gtaaccagga aaatcactgc cggctagtcc      2400
caagcaaacg ggctaggagg aaagattaaa aaaacaacaa caacaactta tttagtttgg      2460
ggaggggaag catttttaag tgtgttgtaa aatcaaattt tatatttcat tttttgactc      2520
ttgaaaaatg tctttgctcc ttggcagcta ccagcagaga ctctatagct gtctcttagg      2580
gcagtatttt ggggaagtgg ggcttgaaga agcagcctaa tgaaccaaca taccgttttg      2640
tgtgtggttt ttttgtttg tttgtttgtt tgttttgaga cagagtcttg ctctgtcacc        2700
caggctggag tgcagtgaca tgatcttagc tcactgcaac ctccgcctcc tgggttcaag      2760
tgattctcct gcctcagcct cccaagtagc tgggattact ggtgcacacc accacactca      2820
gctaattttt gcattttag tagagatggg gtttcaccat gttggccagg ctggtctcga       2880
actcctggac ttaagtgagc ctcccgcctc agtctcccaa agcgctggga ttgcaggcag      2940
gagccactga gcccagccaa gacttcagtg ttgactgctt tggaggcaca aacccatgca      3000
agcgttagtt ccaaagttca gtgtgtaccc ttaaatgaac aatgaagcag gtaaaattac      3060
ccttgaaaaa aatcccttgg accacccata aatgacagtg acttttcaa tatggactca      3120 tcatagccag ttttccttt gaagttggaa ctgatcaccc ttttgtcatc tgtaccagat       3180
cagtagttgg cttgtgttac attttgtgtg tgtgtgtgcg tgttttaaac cagtgcatat     3240
aaattgtatg ttaaatgtaa gtaactttaa gttgacttat ctcttcacag taatcaagcc     3300
tcacgtaatt catgcttttt aaattcagcc agccccccct ctctgaaatt ttattatgta      3360
aataatttgt gttccctgat cactcgttta agttcttagt tgtatgtcat ctcttctcta     3420
gcaggaattg gcaaactttt ttgtaaaggg gtagaaagtg aagattttag gctttgcagg     3480
ccatatagcc tctgctgcaa atgctcagcc ctgctgttgt aatgtaaaag ctgccacaga      3540
cactacatga acacgaatga gtgtggctgg tgttccaata aaactttatt tacacaaaaa     3600
aaaaaaaaaa                                                             3610
```

<210> SEQ ID NO 5
<211> LENGTH: 3599
<212> TYPE: DNA
<213> ORGANISM: Homo sapiens

<400> SEQUENCE: 5

```
ggcccctgcg cccttcctgg gatcactccg actgccccgc gcctctgcca actcctctgg       60
accctcgcgg ccgtgggcag cggctgccgc gcctgtctgc ccgagggagg accttcgcct      120
ctgcatttgt ccagtaactc tggctgtgcc ggatactgct tgggtaaaac gggcacccca      180
ggaacatggc agacgaagat ctcatcttcc gcctggaagg cgttgatggc ggccagtccc      240
cccgagctgg ccatgatggt gattctgatg gggacagcga cgatgaggaa ggttacttca      300
tctgccccat cacggatgac ccaagctcga accagaatgt caattccaag gttaataagt      360
actacagcaa cctaacaaaa agtgagcggt atagctccag cgggtccccg gcaaactcct      420
tccacttcaa ggaagcctgg aagcacgcaa tccagaaggc caagcacatg cccgacccct      480
gggctgagtt ccacctggaa gatattgcca ccgaacgtgc tactcgacac aggtacaacg      540
ccgtcaccgg ggaatggctg gatgatgaag ttctgatcaa gatggcatct cagcccttcg      600
gccgaggagc aatgagggag tgcttccgga cgaagaagct ctccaacttc ttgcatgccc      660
agcagtggaa gggcgcctcc aactacgtgg cgaagcgcta catcgagccc gtagaccggg      720
atgtgtactt tgaggacgtg cgtctacaga tggaggccaa gctctggggg gaggagtata      780
atcggcacaa gccccccaag caggtggaca tcatgcagat gtgcatcatc gagctgaagg      840
```

```
acagaccggg caagcccctc ttccacctgg agcactacat cgagggcaag tacatcaagt    900
acaactccaa ctctggcttt gtccgcgatg acaaacatcc cctgacgccg caggccttca    960
gccacttcac ttttgagcgt tccggccatc agctgatagt ggtggacatc cagggagttg   1020
gggatctcta cactgaccca cagatccaca cggagacggg cactgacttt ggagacggca   1080
acctaggtgt ccgcgggatg gcgctcttct tctactctca tgcctgcaac cggatttgcg   1140
agagcatggg ccttgctccc tttgacctct cgccccggga gagggatgca gtgaatcaga   1200
acaccaagct gctgcaatca gccaagacca tcttgagagg aacagaggaa aaatgtggga   1260
gcccccgagt aaggaccctc tctgggagcc ggccacccct gctccgtccc ctttcagaga   1320
actctggaga cgagaacatg agcgacgtga ccttcgactc tctcccttct tccccatctt   1380
cggccacacc acacagccag aagctagacc acctccattg gccagtgttc agtgacctcg   1440
ataacatggc atccagagac catgatcatc tagacaacca ccgggagtct gagaatagtg   1500
gggacagcgg atacccccagt gagaagcggg gtgagctgga tgaccctgag ccccgagaac   1560
atggccactc atacagtaat cggaagtacg agtctgacga agacagcctg gcagctctg   1620 gacgggtatg tgtagagaag tggaatctcc tcaactcctc ccgcctccac ctgccgaggg   1680
cttcggccgt ggccctggaa gtgcaaaggc ttaatgctct ggacctcgaa aagaaaatcg   1740
ggaagtccat tttggggaag gtccatctgg ccatggtgcg ctaccacgag ggtgggcgct   1800
tctgcgagaa gggcgaggag tgggaccagg agtcggctgt cttccacctg gagcacgcag   1860
ccaacctggg cgagctggag gccatcgtgg gcctgggact catgtactcg cagttgcctc   1920
atcacatcct agccgatgtc tctctgaagg agacagaaga gaacaaaacc aaaggatttg   1980
attacttact aaaggccgct gaagctggcg acaggcagtc catgatccta gtggcgcgag   2040
cttttgactc tggccagaac ctcagcccgg acaggtgcca agactggcta gaggccctgc   2100
actggtacaa cactgccctg gagatgacgg actgtgatga gggcggtgag tacgacggaa   2160
tgcaggacga gccccggtac atgatgctgg ccagggaggc cgagatgctg ttcacaggag   2220
gctacgggct ggagaaggac ccgcagagat caggggactt gtatacccag gcagcagagg   2280
cagcgatgga agccatgaag ggccgactgg ccaaccagta ctaccaaaag gctgaagagg   2340
cctgggccca gatggaggag taaccaggaa aatcactgcc ggctagtccc aagcaaacgg   2400
gctaggagga aagattaaaa aaacaacaac aacaacttat ttagtttggg gaggggaagc   2460
atttttaagt gtgttgtaaa atcaaatttt atatttcatt ttttgactct tgaaaaatgt   2520
ctttgctcct tggcagctac cagcagagac tctatagctg tctcttaggg cagtattttg   2580
gggaagtggg gcttgaagaa gcagcctaat gaaccaacat accgttttgt gtgtggtttt   2640
ttttgtttgt ttgtttgttt gttttgagac agagtcttgc tctgtcaccc aggctggagt   2700
gcagtgacat gatcttagct cactgcaacc tccgcctcct gggttcaagt gattctcctg   2760
cctcagcctc ccaagtagct gggattactg gtgcacacca ccacactcag ctaattttg    2820 catttttagt agagatgggg tttcaccatg ttggccaggc tggtctcgaa ctcctggact   2880
taagtgagcc tcccgcctca gtctcccaaa gcgctgggat tacaggcagg agccactgag   2940
cccagccaag acttcagtgt tgactgcttt ggaggcacaa acccatgcaa gcgttagttc   3000
caaagttcag tgtgtacccct taaatgaaca atgaagcagg taaaattacc cttgaaaaaa   3060
atcccttgga ccacccataa atgacagtga ctttttcaat atggactcat catagccagt   3120 ttccttttg aagttggaac tgatcaccct tttgtcatct gtaccagatc agtagttggc    3180
ttgtgttaca ttttgtgtgt gtgtgtgcgt gttttaaacc agtgcatata aattgtatgt   3240
```

```
taaatgtaag taactttaag ttgacttatc tcttcacagt aatcaagcct cacgtaattc    3300
atgcttttta aattcagcca gccccccctc tctgaaattt tattatgtaa ataatttgtg    3360
ttccctgatc actcgtttaa gttcttagtt gtatgtcatc tcttctctag caggaattgg    3420
caaacttttt tgtaaagggg tagaaagtga agattttagg ctttgcaggc catatagcct    3480
ctgctgcaaa tgctcagccc tgctgttgta atgtaaaagc tgccacagac actacatgaa    3540
cacgaatgag tgtggctggt gttccaataa aactttattt acacaaaaaa aaaaaaaaa    3599
```

```
<210> SEQ ID NO 6
<211> LENGTH: 19
<212> TYPE: RNA
<213> ORGANISM: Artificial
<220> FEATURE:
<223> OTHER INFORMATION: Synthetic

<400> SEQUENCE: 6
cgaagaagcu cuccaacuu                                                 19

<210> SEQ ID NO 7
<211> LENGTH: 19
<212> TYPE: RNA
<213> ORGANISM: Artificial
<220> FEATURE:
<223> OTHER INFORMATION: synthetic

<400> SEQUENCE: 7
ggauggcucu cuucuucua                                                 19

<210> SEQ ID NO 8
<211> LENGTH: 19
<212> TYPE: RNA
<213> ORGANISM: Artificial
<220> FEATURE:
<223> OTHER INFORMATION: synthetic

<400> SEQUENCE: 8
gaacauggcc acucauaca                                                 19

<210> SEQ ID NO 9
<211> LENGTH: 19
<212> TYPE: RNA
<213> ORGANISM: Artificial
<220> FEATURE:
<223> OTHER INFORMATION: synthetic

<400> SEQUENCE: 9
gcaguugccu caucacauc                                                 19
```

EEF2K AS MODIFIERS OF THE PTEN/AKT PATHWAY AND METHODS OF USE

This application is a national stage application of International Application No. PCT/US06/08675 filed Mar. 10, 2006, which claims priority to U.S. provisional application Ser. No. 60/660,207 filed Mar. 10, 2005, both of which are herein incorporated by reference in their entireties.

The computer readable form of the sequence listing, "05-968-C-WO-US_SEQLIST.TXT" [22,244 bytes] is hereby incorporated by reference.

BACKGROUND OF THE INVENTION

Intracellular levels of phosphorylation are regulated by the coordinated action of protein kinases and phosphatases. Somatic mutations in the PTEN (Phosphatase and Tensin homolog deleted on chromosome 10) gene are known to cause tumors in a variety of human tissues. In addition, germline mutations in PTEN are the cause of human diseases (Cowden disease and Bannayan-Zonana syndrome) associated with increased risk of breast and thyroid cancer (Nelen M R et al. (1997) Hum Mol Genet, 8:1383-1387; Liaw D et al. (1997) Nat Genet, 1:64-67; Marsh D J et al. (1998) Hum Mol Genet, 3:507-515). PTEN acts as a tumor suppressor by regulating several signaling pathways through the second messenger phosphatidylinositol 3,4,5 triphosphate (PIP3). PTEN dephosphorylates the D3 position of PIP3 and downregulates signaling events dependent on PIP3 levels (Maehama T and Dixon J E (1998) J Biol Chem, 22, 13375-8). This inhibits downstream targets mainly protein kinase B (PKB/AKT). PTEN sequence is conserved in evolution, and exists in mouse (Hansen G M and Justice M J (1998) Mamm Genome, 9(1):88-90), *Drosophila* (Goberdhan D C et al (1999) Genes and Dev, 24:3244-58; Huang H et al (1999) Development 23:5365-72), and *C. elegans* (Ogg S and Ruvkun G, (1998) Mol Cell, (6):887-93). Studies in these model organisms have helped to elucidate the role of PTEN in processes relevant to tumorigenesis. In *Drosophila*, the PTEN homolog (dPTEN) has been shown to regulate cell size, survival, and proliferation (Huang et al, supra; Goberdhan et al, supra; Gao X et al, 2000, 221:404-418). In mice, loss of PTEN function increases cancer susceptibility (Di Cristofano A et al (1998) Nature Genetics, 19:348-355; Suzuki A et al (1998) Curr. Biol., 8:1169-78).

AKT signaling is frequently hyperactivated by a variety of mechanisms in a wide range of human cancers, including melanoma, breast, lung, prostate, and ovarian tumors (see Vivanco I and Sawyers C L (2002) Nat Rev Cancer. 2(7):489-501; Scheid M P and Woodgett J R (2001) J Mammary Gland Biol Neoplasia. 6(1):83-99). In tumor cells, the AKT protein kinase activity can be elevated by amplification and overexpression of the AKT2 gene, or by increased production of phosphatidylinositol (3, 4, 5) trisphosphate (PIP3), which activates AKT by recruitment to the plasma membrane. In normal phosphoinositide metabolism, phosphatidylinositol (3, 4) bisphosphate (PIP2) is phosphorylated by phosphatidylinositol 3-kinase (PI3K) to generate PIP3, and PIP3 is dephosphorylated back to PIP2 by the lipid phosphatase PTEN. Most commonly, however, PIP3 levels in tumor cells are elevated by mutation or deletion of the PTEN tumor suppressor, at rates as high as 40-50% of prostate cancers.

The PTEN/AKT pathway promotes tumor progression by enhancing cell proliferation, growth, survival, and motility, and by suppressing apoptosis. These effects are mediated by several AKT substrates, including the related transcription factors FKHR and AFX, for which phosphorylation by AKT mediates nuclear export. Signaling through the TOR (mTOR) branch of the PTEN/AKT signaling pathway regulates protein synthesis, which is directly involved in the growth activation and cellular transformation properties of AKT signaling. TOR directly phosphorylates several targets including 4EBP1 and p70S6 kinase. p70S6 kinase directly phosphorylates ribosomal protein S6 (RPS6) (Bader A G et al. (2004) Oncogene 23:3145-3150; Hay N et al. (2004) Genes Dev. 18:1926-1945). Additional direct AKT substrates have been identified which can serve as a readout for PTEN/AKT signaling activity, including the protein PRAS40 (Kovacina K S et al. (2003) JBC 278(12): 10189-10194).

Identification of the involvement of novel genes in particular pathways, such as disease pathways, and their function in such pathways can directly contribute to the understanding of modulation of these pathways. Further, the identified genes may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the PTEN/AKT pathway in human cells, hereinafter referred to as MODIFIER OF PTEN/AKT (MPTENAKT). Specifically, we have identified one gene, Eukaryotic Elongation Factor 2 Kinase (EFF2K) modifies the PTEN/AKT pathway in a number of human tissues and cell lines. The EFF2K gene is expressed in many standard tumor cell lines. The EEF2K kinase is a $Ca^{++}$/Calmodulin dependent protein kinase that phosporolates eEF2 at Threonine 56 to inhibit translation. The kinase is regulated by multiple pathways by phosphorylation. Its activity is highly upregulated in some tumors. EEF2K antagonists inhibit cell growth and cause cell cycle arrest at the G1 phase of the cell cycle. The invention provides methods for utilizing these PTEN/AKT modifier genes and polypeptides to identify EEF2K-modulating agents that are candidate therapeutic agents that can be used in the treatment of disorders associated with defective or impaired PTEN/AKT function and/or EEF2K function. Preferred EEF2K-modulating agents specifically bind to EEF2K polypeptides and restore PTEN/AKT function. Other preferred EEF2K-modulating agents are nucleic acid modulators such as antisense oligomers and RNAi that repress EEF2K gene expression or product activity by, for example, binding to and inhibiting the respective nucleic acid (i.e. DNA or mRNA).

EEF2K modulating agents may be evaluated by any convenient in vitro or in vivo assay for molecular interaction with an EEF2K polypeptide or nucleic acid. In one embodiment, candidate EEF2K modulating agents are tested with an assay system comprising an EEF2K polypeptide or nucleic acid. Agents that produce a change in the activity of the assay system relative to controls are identified as candidate PTEN/AKT modulating agents. The assay system may be cell-based or cell-free. EEF2K-modulating agents include EEF2K related proteins (e.g. dominant negative mutants, and biotherapeutics); EEF2K-specific antibodies; EEF2K-specific antisense oligomers and other nucleic acid modulators; and chemical agents that specifically bind to or interact with EEF2K or compete with EEF2K binding partner (e.g. by binding to an EEF2K binding partner). In one specific embodiment, a small molecule modulator is identified using a binding assay. In specific embodiments, the screening assay system is selected from an apoptosis assay, a cell proliferation assay, an angiogenesis assay, and a hypoxic induction assay.

In another embodiment, candidate PTEN/AKT pathway modulating agents are further tested using a second assay system that detects changes in the PTEN/AKT pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the PTEN/AKT pathway, such as an angiogenic, apoptotic, or cell proliferation disorder (e.g. cancer).

The invention further provides methods for modulating the EEF2K function and/or the PTEN/AKT pathway in a mammalian cell by contacting the mammalian cell with an agent that specifically binds an EEF2K polypeptide or nucleic acid. The agent may be a small molecule modulator, a nucleic acid modulator, or an antibody and may be administered to a mammalian animal predetermined to have a pathology associated with the PTEN/AKT pathway.

DETAILED DESCRIPTION OF THE INVENTION

We designed a genetic screen to identify suppressors genes that when inactivated, decrease signaling through the PTEN/AKT pathway. Several genes were identified including EEF2K. Accordingly, these EEF2K genes (i.e., nucleic acids and polypeptides) are attractive drug targets for the treatment of pathologies associated with a defective PTEN/AKT signaling pathway, such as cancer. Table 1 (Example II) lists these genes.

In vitro and in vivo methods of assessing EEF2K function are provided herein. Modulation of the EEF2K or their respective binding partners is useful for understanding the association of the PTEN/AKT pathway and its members in normal and disease conditions and for developing diagnostics and therapeutic modalities for PTEN/AKT related pathologies. EEF2K-modulating agents that act by inhibiting or enhancing EEF2K expression, directly or indirectly, for example, by affecting an EEF2K function such as enzymatic (e.g., catalytic) or binding activity, can be identified using methods provided herein. EEF2K modulating agents are useful in diagnosis, therapy and pharmaceutical development.

Nucleic Acids and Polypeptides of the Invention

Sequences related to EEF2K nucleic acids and polypeptides that can be used in the invention are disclosed in Genbank (referenced by Genbank identifier (GI) or RefSeq number), shown in Table 1 and in the appended sequence listing. The human EEF2K gene encodes a 725 amino acid protein that contains an alpha kinase domain approximately between amino acids 125 and 325. This domain contains a TPR repeat and the kinase is in the SEL-1 subfamily of kinases. The next most closely related kinase is only 28% identical in the kinase domain. The protein also contains a COG0790 domain at approximately amino acids 500 to 710.

The term "EEF2K polypeptide" refers to a full-length EEF2K protein or a functionally active fragment or derivative thereof. A "functionally active" EEF2K fragment or derivative exhibits one or more functional activities associated with a full-length, wild-type EEF2K protein, such as antigenic or immunogenic activity, enzymatic activity, ability to bind natural cellular substrates, etc. The functional activity of EEF2K proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active EEF2K polypeptide is an EEF2K derivative capable of rescuing defective endogenous EEF2K activity, such as in cell based or animal assays; the rescuing derivative may be from the same or a different species. For purposes herein, functionally active fragments also include those fragments that comprise one or more structural domains of an EEF2K, such as a kinase domain or a binding domain. Protein domains can be identified using the PFAM program (Bateman A., et al., Nucleic Acids Res, 1999, 27:260-2). Methods for obtaining EEF2K polypeptides are also further described below. In some embodiments, preferred fragments are functionally active, domain-containing fragments comprising at least 25 contiguous amino acids, preferably at least 50, more preferably 75, and most preferably at least 100 contiguous amino acids of an EEF2K. In further preferred embodiments, the fragment comprises the entire functionally active domain.

The term "EEF2K nucleic acid" refers to a DNA or RNA molecule that encodes an EEF2K polypeptide. Preferably, the EEF2K polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human EEF2K. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein.; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of an EEF2K. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of an EEF2K under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of EEF2K Nucleic Acids and Polypeptides EEF2K nucleic acids and polypeptides are useful for identifying and testing agents that modulate EEF2K function and for other applications related to the involvement of EEF2K in the PTEN/AKT pathway. EEF2K nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of an EEF2K protein for assays used to assess EEF2K function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant EEF2K is expressed in a cell line known to have defective PTEN/AKT function. The recombinant cells are used in cell-based screening assay systems of the invention, as described further below.

The nucleotide sequence encoding an EEF2K polypeptide can be inserted into any appropriate expression vector. The necessary transcriptional and translational signals, including promoter/enhancer element, can derive from the native EEF2K gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the EEF2K gene product, the expression vector can comprise a promoter operably linked to an EEF2K gene nucleic acid, one or more origins of replication, and, one or more selectable markers (e.g. thymidine kinase activity, resistance to antibiotics, etc.). Alternatively, recombinant expression vectors can be identified by assaying for the expression of the EEF2K gene product based on the physical or functional properties of the EEF2K protein in in vitro assay systems (e.g. immunoassays).

The EEF2K protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the EEF2K gene sequence is identified, the gene product can be isolated and purified using standard methods (e.g. ion exchange, affinity, and gel exclusion chromatography; centrifugation; differential solubility; electrophoresis). Alternatively, native EEF2K proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of EEF2K or other genes associated with the PTEN/AKT pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter EEF2K expression may be used in in vivo assays to test for activity of a candidate PTEN/AKT modulating agent, or to further assess the role of EEF2K in a PTEN/AKT pathway process such as apoptosis or cell proliferation. Preferably, the altered EEF2K expression results in a detectable phenotype, such as decreased or increased levels of cell proliferation, angiogenesis, or apoptosis compared to control animals having normal EEF2K expression. The genetically modified animal may additionally have altered PTEN or AKT expression (e.g. PTEN or AKT knockout). Preferred genetically modified animals are mammals such as primates, rodents (preferably mice or rats), among others. Preferred non-mammalian species include zebrafish, C. elegans, and Drosophila. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic Drosophila see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous EEF2K gene that results in a decrease of EEF2K function, preferably such that EEF2K expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse EEF2K gene is used to construct a homologous recombination vector suitable for altering an endogenous EEF2K gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the EEF2K gene, e.g., by introduction of additional copies of EEF2K, or by operatively inserting a regulatory sequence that provides for altered expression of an endogenous copy of the EEF2K gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the PTEN/AKT pathway, as animal models of disease and disorders implicating defective PTEN/AKT function, and for in vivo testing of candidate therapeutic agents, such as those identified in screens described below. The candidate therapeutic agents are administered to a genetically modified animal having altered EEF2K function and phenotypic changes are compared with appropriate control animals such as genetically modified animals that receive placebo treatment, and/or animals with unaltered EEF2K expression that receive candidate therapeutic agent. In addition to the above-described genetically modified animals having altered EEF2K function, animal models having defective PTEN or AKT function (and otherwise normal EEF2K function), can be used in the methods of the present invention. For example, a mouse with defective PTEN or AKT function can be used to assess, in vivo, the activity of a candidate PTEN/AKT modulating agent identified in one of the in vitro assays described below. Transgenic mice with defective PTEN function have been described in literature (Di Cristofano et al, supra). Transgenic mice with defective AKT function have also been described (Chen, W. S. et al (2001) Genes Dev. 15: 2203-2208; Condorelli, G. et al (2002) Proc. Nat. Acad. Sci. 99: 12333-12338; Peng, X. et al (2003) Genes Dev. 17: 1352-1365). Preferably, the candidate PTEN/AKT modulating agent when administered to a model system with cells defective in PTEN/AKT function, produces a detectable phenotypic change in the model system indicating that the PTEN/AKT function is restored, i.e., the cells exhibit normal cell cycle progression.

Modulating Agents

The invention provides methods to identify agents that interact with and/or modulate the function of EEF2K and/or the PTEN/AKT pathway. Modulating agents identified by the methods are also part of the invention. Such agents are useful in a variety of diagnostic and therapeutic applications associated with the PTEN/AKT pathway, as well as in further analysis of the EEF2K protein and its contribution to the PTEN/AKT pathway. Accordingly, the invention also provides methods for modulating the PTEN/AKT pathway comprising the step of specifically modulating EEF2K activity by administering an EEF2K-interacting or -modulating agent.

As used herein, an "EEF2K-modulating agent" is any agent that modulates EEF2K function, for example, an agent that interacts with EEF2K to inhibit or enhance EEF2K activity or otherwise affect normal EEF2K function. EEF2K function can be affected at any level, including transcription, protein expression, protein localization, and cellular or extracellular activity. In a preferred embodiment, the EEF2K-modulating agent specifically modulates the function of the EEF2K. The phrases "specific modulating agent", "specifically modulates", etc., are used herein to refer to modulating agents that directly bind to the EEF2K polypeptide or nucleic acid, and preferably inhibit, enhance, or otherwise alter, the function of the EEF2K. These phrases also encompass modulating agents that alter the interaction of the EEF2K with a binding partner, substrate, or cofactor (e.g. by binding to a binding partner of an EEF2K, or to a protein/binding partner complex, and altering EEF2K function). In a further preferred embodiment, the EEF2K-modulating agent is a modulator of the PTEN/AKT pathway (e.g. it restores and/or upregulates PTEN/AKT function) and thus is also a PTEN/AKT-modulating agent.

Preferred EEF2K-modulating agents include small molecule compounds; EEF2K-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $19^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the EEF2K protein or may be identified by screening compound libraries. Alternative appropriate modulators of this class are natural products, particularly secondary metabolites from organisms such as plants or fungi, which can also be identified by screening compound libraries for EEF2K-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the PTEN/AKT pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific EEF2K-interacting proteins are useful in a variety of diagnostic and therapeutic applications related to the PTEN/AKT pathway and related disorders, as well as in validation assays for other EEF2K-modulating agents. In a preferred embodiment, EEF2K-interacting proteins affect normal EEF2K function, including transcription, protein expression, protein localization, and cellular or extra-cellular activity. In another embodiment, EEF2K-interacting proteins are useful in detecting and providing information about the function of EEF2K proteins, as is relevant to PTEN/AKT related disorders, such as cancer (e.g., for diagnostic means).

An EEF2K-interacting protein may be endogenous, i.e. one that naturally interacts genetically or biochemically with an EEF2K, such as a member of the EEF2K pathway that modulates EEF2K expression, localization, and/or activity. EEF2K-modulators include dominant negative forms of EEF2K-interacting proteins and of EEF2K proteins themselves. Yeast two-hybrid and variant screens offer preferred methods for identifying endogenous EEF2K-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928, 868). Mass spectrometry is an alternative preferred method for the elucidation of protein complexes (reviewed in, e.g., Pandley A and Mann M, Nature (2000) 405:837-846; Yates J R $3^{rd}$, Trends Genet (2000) 16:5-8).

An EEF2K-interacting protein may be an exogenous protein, such as an EEF2K-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). EEF2K antibodies are further discussed below.

In preferred embodiments, an EEF2K-interacting protein specifically binds an EEF2K protein. In alternative preferred embodiments, an EEF2K-modulating agent binds an EEF2K substrate, binding partner, or cofactor.

Antibodies

In another embodiment, the protein modulator is an EEF2K specific antibody agonist or antagonist. The antibodies have therapeutic and diagnostic utilities, and can be used in screening assays to identify EEF2K modulators. The antibodies can also be used in dissecting the portions of the EEF2K pathway responsible for various cellular responses and in the general processing and maturation of the EEF2K.

Antibodies that specifically bind EEF2K polypeptides can be generated using known methods. Preferably the antibody is specific to a mammalian ortholog of EEF2K polypeptide, and more preferably, to human EEF2K. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of EEF2K which are particularly antigenic can be selected, for example, by routine screening of EEF2K polypeptides for antigenicity or by applying a theoretical method for selecting antigenic regions of a protein (Hopp and Wood (1981), Proc. Nati. Acad. Sci. U.S.A. 78:3824-28; Hopp and Wood, (1983) Mol. Immunol. 20:483-89; Sutcliffe et al., (1983) Science 219:660-66) to the amino acid sequence of an EEF2K. Monoclonal antibodies with affinities of $10^9 M^{-1}$ preferably $10^9 M^{-1}$ to $10^{10} M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618, 577). Antibodies may be generated against crude cell extracts of EEF2K or substantially purified fragments thereof. If EEF2K fragments are used, they preferably comprise at least 10, and more preferably, at least 20 contiguous amino acids of an EEF2K protein. In a particular embodiment, EEF2K-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of EEF2K-specific antibodies is assayed by an appropriate assay such as a solid phase enzyme-linked immunosorbant assay (ELISA) using immobilized corresponding EEF2K polypeptides. Other assays, such as radioimmunoassays or fluorescent assays might also be used.

Chimeric antibodies specific to EEF2K polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

EEF2K-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859, 206; WO0073469).

Specific Biotherapeutics

In a preferred embodiment, an EEF2K-interacting protein may have biotherapeutic applications. Biotherapeutic agents formulated in pharmaceutically acceptable carriers and dosages may be used to activate or inhibit signal transduction pathways. This modulation may be accomplished by binding a ligand, thus inhibiting the activity of the pathway; or by binding a receptor, either to inhibit activation of, or to activate, the receptor. Alternatively, the biotherapeutic may itself be a ligand capable of activating or inhibiting a receptor. Biotherapeutic agents and methods of producing them are described in detail in U.S. Pat. No. 6,146,628.

When the EEF2K is a ligand, it may be used as a biotherapeutic agent to activate or inhibit its natural receptor. Alternatively, antibodies against EEF2K, as described in the previous section, may be used as biotherapeutic agents.

When the EEF2K is a receptor, its ligand(s), antibodies to the ligand(s) or the EEF2K itself may be used as biotherapeutics to modulate the activity of EEF2K in the PTEN/AKT pathway.

Nucleic Acid Modulators

Other preferred EEF2K-modulating agents comprise nucleic acid molecules, such as antisense oligomers or double stranded RNA (dsRNA), which generally inhibit EEF2K activity. Preferred nucleic acid modulators interfere with the function of the EEF2K nucleic acid such as DNA replication, transcription, translocation of the EEF2K RNA to the site of protein translation, translation of protein from the EEF2K RNA, splicing of the EEF2K RNA to yield one or more mRNA species, or catalytic activity which may be engaged in or facilitated by the EEF2K RNA.

In one embodiment, the antisense oligomer is an oligonucleotide that is sufficiently complementary to an EEF2K mRNA to bind to and prevent translation, preferably by binding to the 5' untranslated region. EEF2K-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.:7:187-95; U.S. Pat. No. 5,235,033; and U.S. Pat No. 5,378,841).

Alternative preferred EEF2K nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498; Novina C D and Sharp P. 2004 Nature 430:161-164; Soutschek J et al 2004 Nature 432:173-178; Hsieh A C et al. (2004) NAR 32(3):893-901).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, an EEF2K-specific nucleic acid modulator is used in an assay to further elucidate the role of the EEF2K in the PTEN/AKT pathway, and/or its relationship to other members of the pathway. In another aspect of the invention, an EEF2K-specific antisense oligomer is used as a therapeutic agent for treatment of PTEN/AKT-related disease states.

Assay Systems

The invention provides assay systems and screening methods for identifying specific modulators of EEF2K activity. As used herein, an "assay system" encompasses all the components required for performing and analyzing results of an assay that detects and/or measures a particular event. In general, primary assays are used to identify or confirm a modulator's specific biochemical or molecular effect with respect to the EEF2K nucleic acid or protein. In general, secondary assays further assess the activity of an EEF2K modulating agent identified by a primary assay and may confirm that the modulating agent affects EEF2K in a manner relevant to the PTEN/AKT pathway. In some cases, EEF2K modulators will be directly tested in a secondary assay.

In a preferred embodiment, the screening method comprises contacting a suitable assay system comprising an EEF2K polypeptide or nucleic acid with a candidate agent under conditions whereby, but for the presence of the agent, the system provides a reference activity (e.g. binding activity), which is based on the particular molecular event the screening method detects. A statistically significant difference between the agent-biased activity and the reference activity indicates that the candidate agent modulates EEF2K activity, and hence the PTEN/AKT pathway. The EEF2K polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of EEF2K and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when EEF2K-interacting proteins are used in screens to identify small molecule modulators, the binding specificity of the interacting protein to the EEF2K protein may be assayed by various known methods such as substrate processing (e.g. ability of the candidate EEF2K-specific binding agents to function as negative effectors in EEF2K-expressing cells), binding equilibrium constants (usually at least about $10^7 M^{-1}$, preferably at least about $10^8 M^{-1}$, more preferably at least about $10^9 M^{-1}$), and immunogenicity (e.g. ability to elicit EEF2K specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of an EEF2K polypeptide, a fusion protein thereof, or to cells or membranes bearing the polypeptide or fusion protein. The EEF2K polypeptide can be full length or a fragment thereof that retains functional EEF2K activity. The EEF2K polypeptide may be fused to another polypeptide, such as a peptide tag for detection or anchoring, or to another tag. The EEF2K polypeptide is preferably human EEF2K, or is an ortholog or derivative thereof as described above. In a preferred embodiment, the screening assay detects candidate agent-based modulation of EEF2K interaction with a binding target, such as an endogenous or exogenous protein or other substrate that has EEF2K-specific binding activity, and can be used to assess normal EEF2K gene function.

Suitable assay formats that may be adapted to screen for EEF2K modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate EEF2K and PTEN/AKT pathway modulators (e.g. U.S. Pat. No. 6,165,992 and U.S. Pat. No. 6,720,162 (kinase assays); U.S. Pat. Nos. 5,550,019 and 6,133,437 (apoptosis assays); U.S. Pat. No. 6,114,132 and U.S. Pat. No. 6,720,162 (phosphatase and protease assays), and U.S. Pat. Nos. 5,976, 782, 6,225,118 and 6,444,434 (angiogenesis assays), among others). Specific preferred assays are described in more detail below.

Protein kinases, key signal transduction proteins that may be either membrane-associated or intracellular, catalyze the transfer of gamma phosphate from adenosine triphosphate (ATP) to a serine, threonine or tyrosine residue in a protein substrate. Radioassays, which monitor the transfer from [gamma-$^{32}$P or -$^{33}$P]ATP, are frequently used to assay kinase activity. For instance, a scintillation assay for p56 (lck) kinase activity monitors the transfer of the gamma phosphate from [gamma-$^{33}$P] ATP to a biotinylated peptide substrate. The substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand. Other assays for protein kinase activity may use antibodies that specifically recognize phosphorylated substrates. For instance, the kinase receptor activation (KIRA) assay measures receptor tyrosine kinase activity by ligand stimulating the intact receptor in cultured cells, then capturing solubilized receptor with specific antibodies and quantifying phosphorylation via phosphotyrosine ELISA (Sadick M D, Dev Biol Stand (1999) 97:121-133). Another example of antibody based assays for protein kinase activity is TRF (time-resolved fluorometry). This method utilizes europium chelate-labeled anti-phosphotyrosine antibodies to detect phosphate transfer to a polymeric substrate coated onto microtiter plate wells. The amount of phosphorylation is then detected using time-resolved, dissociation-enhanced fluorescence (Braunwalder A F, et al., Anal Biochem 1996 Jul. 1; 238(2):159-64). Yet other assays for kinases involve uncoupled, pH sensitive assays that can be used for high-throughput screening of potential inhibitors or for determining substrate specificity. Since kinases catalyze the transfer of a gamma-phosphoryl group from ATP to an appropriate hydroxyl acceptor with the release of a proton, a pH sensitive assay is based on the detection of this proton using an appropriately matched buffer/indicator system (Chapman E and Wong C H (2002) Bioorg Med Chem. 10:551-5).

Protein phosphatases catalyze the removal of a gamma phosphate from a serine, threonine or tyrosine residue in a protein substrate. Since phosphatases act in opposition to kinases, appropriate assays measure the same parameters as kinase assays. In one example, the dephosphorylation of a fluorescently labeled peptide substrate allows trypsin cleavage of the substrate, which in turn renders the cleaved substrate significantly more fluorescent (Nishikata M et al., Biochem J (1999) 343:35-391). In another example, fluorescence polarization (FP), a solution-based, homogeneous technique requiring no immobilization or separation of reaction components, is used to develop high throughput screening (HTS) assays for protein phosphatases. This assay uses direct binding of the phosphatase with the target, and increasing concentrations of target-phosphatase increase the rate of dephosphorylation, leading to a change in polarization (Parker G J et al., (2000) J Biomol Screen 5:77-88).

Glycosyltransferases mediate changes in glycosylation patterns that, in turn, may affect the function of glycoproteins and/or glycolipids and, further downstream, processes of development, differentiation, transformation and cell-cell recognition. An assay for glycosyltransferase uses scintillation methods to measure the transfer of carbohydrate from radiolabeled sugar-nueucleotide donor to a synthetic glycopolymer acceptor that is coupled to polyacrylamide and coated on plastic microtiter plates (Donovan R S et al., Glycoconj J (1999) 16:607-615).

G-protein-coupled receptors (GPCRs) comprise a large family of cell surface receptors that mediate a diverse array of biological functions. They selectively respond to a wide variety of extracellular chemical stimuli to activate specific signaling cascades. Assays may measure reporter gene activity or changes in intracellular calcium ions, or other second messengers (Durocher Y et al., Anal Biochem (2000) 284: 316-326; Miller T R et al., J Biomol Screen (1999) 4:249-258). Such assays may utilize chimeric Ga proteins that will couple to many different GPCRs and thus facilitate "universal" screening assays (Coward P et al., Anal Biochem (1999) 270:242-248; Milligan G and Rees S et al., Trends Pharmacol Sci (1999) 20:118-124).

GPCRs exert their effects through heterotrimeric G proteins, which cycle between active GTP- and inactive GDP-bound forms. Receptors catalyze the activation of G proteins by promoting exchange of GDP for GTP, while G proteins catalyze their own deactivation through their intrinsic GTPase activity. GEFs accelerate GDP dissociation and GTP binding, while GAPs stimulate GTP hydrolysis to GDP. The same assays used to monitor GPCR activity may thus be applied to monitor the activity of GEFs or GAPs. Alternatively, GEF activity may be assayed by the release of labeled GDP from the appropriate GTPase or by the uptake of labelled GTP. GAP activity may be monitored via a GTP hydrolysis assay using labeled GTP (e.g., Jones S et al., Molec Biol Cell (1998) 9:2819-2837).

Transporter proteins carry a range of substrates, including nutrients, ions, amino acids, and drugs, across cell membranes. Assays for modulators of transporters may use labeled substrates. For instance, exemplary high throughput screens to identify compounds that interact with different peptide and anion transporters both use fluorescently labeled substrates; the assay for peptide transport additionally uses multiscreen filtration plates (Blevitt J M et al., J Biomol Screen 1999, 4:87-91; Cihlar T and Ho E S, Anal Biochem 2000, 283:49-55).

Apoptosis Assays.

Apoptosis or programmed cell death is a suicide program is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumalation in the cytoplasm. Nucleosomes are not present in the cytoplasmic fraction of cells that are not undergoing apoptosis. The Phosphohistone H2B assay is another apoptosis assay, based on phosphorylation of histone H2B as a result of apoptosis. Fluorescent dyes that are associated with phosphohistone H2B may be used to measure the increase of phosphohistone H2B as a result of apoptosis. Apoptosis assays that simultaneously measure multiple parameters associated with apoptosis have also been developed. In such assays, various cellular parameters that can be associated with antibodies or fluorescent dyes, and that mark various stages of apoptosis are labeled, and the results are measured using instruments such as Cellomics™ ArrayScan® HCS System. The measurable parameters and their markers include anti-active caspase-3 antibody which marks intermediate stage apoptosis, anti-PARP-p85 antibody (cleaved PARP) which marks late stage apoptosis, Hoechst labels which label the nucleus and are used to measure nuclear swelling as a measure of early apoptosis and nuclear condensation as a measure of late apoptosis, TOTO-3 fluorescent dye which labels DNA of dead cells with high cell membrane permeability, and anti-alpha-tubulin or F-actin labels, which assess cytoskeletal changes in cells and correlate well with TOTO-3 label.

An apoptosis assay system may comprise a cell that expresses an EEF2K, and that optionally has defective PTEN or AKT function (e.g. PTEN or AKT is over-expressed or under-expressed relative to wild-type cells). A test agent can be added to the apoptosis assay system and changes in induction of apoptosis relative to controls where no test agent is added, identify candidate PTEN/AKT modulating agents. In some embodiments of the invention, an apoptosis assay may be used as a secondary assay to test a candidate PTEN/AKT modulating agents that is initially identified using a cell-free assay system. An apoptosis assay may also be used to test whether EEF2K function plays a direct role in apoptosis. For example, an apoptosis assay may be performed on cells that over- or under-express EEF2K relative to wild type cells. Differences in apoptotic response compared to wild type cells suggests that the EEF2K plays a direct role in the apoptotic response. Apoptosis assays are described further in U.S. Pat. No. 6,133,437.

Cell Proliferation and Cell Cycle Assays.

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specfic to the phosphorylated form of the serine 10 residue of histone H3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 96® AQueous Non-Radioactive Cell Proliferation Assay (Cat.#G5421).

Cell proliferation may also be assayed by colony formation in soft agar, or clonogenic survival assay (Sambrook et al., Molecular Cloning, Cold Spring Harbor (1989)). For example, cells transformed with EEF2K are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with an EEF2K may be stained with propidium iodide and evaluated in a flow cytometer (available from Becton Dickinson), which indicates accumulation of cells in different stages of the cell cycle.

Involvement of a gene in cell cycle may also be assayed by FOXO nuclear translocation assays. The FOXO family of transcription factors are mediators of various cellular functions including cell cycle progression and cell death, and are negatively regulated by activation of the PI3 kinase pathway. Akt phosphorylation of FOXO family members leads to FOXO sequestration in the cytoplasm and transcriptional inactivation (Medema, R. H et al (2000) Nature 404: 782-787). PTEN is a negative regulator of PI3 kinase pathway. Activation of PTEN, or loss of PI3 kinase or AKT, prevents phosphorylation of FOXO, leading to accumulation of FOXO in the nucleus, transcriptional activation of FOXO regulated genes, and apoptosis. Alternatively, loss of PTEN leads to pathway activation and cell survival (Nakamura, N. et al (2000) Mol Cell Biol 20: 8969-8982). FOXO translocation into the cytoplasm is used in assays and screens to identify members and/or modulators of the PTEN pathway. FOXO translocation assays using GFP or luciferase as detection reagents are known in the art (e.g., Zhang X et al (2002) J Biol Chem 277:45276-45284; and Li et al (2003) Mol Cell Biol 23:104-118).

Accordingly, a cell proliferation or cell cycle assay system may comprise a cell that expresses an EEF2K, and that optionally has defective PTEN or AKT function (e.g. PTEN or AKT is over-expressed or under-expressed relative to wild-type cells). A test agent can be added to the assay system and changes in cell proliferation or cell cycle relative to controls where no test agent is added, identify candidate PTEN/AKT modulating agents. In some embodiments of the invention, the cell proliferation or cell cycle assay may be used as a secondary assay to test a candidate PTEN/AKT modulating agents that is initially identified using another assay system such as a cell-free assay system. A cell proliferation assay may also be used to test whether EEF2K function plays a direct role in cell proliferation or cell cycle. For example, a cell proliferation or cell cycle assay may be performed on cells that over- or under-express EEF2K relative to wild type cells. Differences in proliferation or cell cycle compared to wild type cells suggests that the EEF2K plays a direct role in cell proliferation or cell cycle.

Angiogenesis.

Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon ITFS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses an EEF2K, and that optionally has defective PTEN or AKT function (e.g. PTEN or AKT is over-expressed or under-expressed relative to wild-type cells). A test agent can be added to the angiogenesis assay system and changes in angiogenesis relative to controls where no test agent is added, identify candidate PTEN/AKT modulating agents. In some embodiments of the invention, the angiogenesis assay may be used as a secondary assay to test a candidate PTEN/AKT modulating agents that is initially identified using another assay system. An angiogenesis assay may also be used to test whether EEF2K function plays a direct role in cell proliferation. For example, an angiogenesis assay may be performed on cells that over- or under-express EEF2K relative to wild type cells. Differences in angiogenesis compared to wild type cells suggests that the EEF2K plays a direct role in angiogenesis. U.S. Pat. Nos. 5,976,782, 6,225,118 and 6,444,434, among others, describe various angiogenesis assays.

Hypoxic Induction.

The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with EEF2K in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses an EEF2K, and that optionally has defective PTEN or AKT function (e.g. PTEN or AKT is over-expressed or under-expressed relative to wild-type cells). A test agent can be added to the hypoxic induction assay system and changes in hypoxic response relative to controls where no test agent is added, identify candidate PTEN/AKT modulating agents. In some embodiments of the invention, the hypoxic induction assay may be used as a secondary assay to test a candidate PTEN/AKT modulating agents that is initially identified using another assay system. A hypoxic induction assay may also be used to test whether EEF2K function plays a direct role in the hypoxic response. For example, a hypoxic induction assay may be performed on cells that over- or under-express EEF2K relative to wild type cells. Differences in hypoxic response compared to wild type cells suggests that the EEF2K plays a direct role in hypoxic induction.

Cell Adhesion.

Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, appropriate primary assays test is a binding assay that tests the antibody's affinity to and specificity for the EEF2K protein. Methods for testing antibody affinity and specificity are well known in the art (Harlow and Lane, 1988, 1999, supra). The enzyme-linked immunosorbant assay (ELISA) is a preferred method for detecting EEF2K-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance EEF2K gene expression, preferably mRNA expression. In general, expression analysis comprises comparing EEF2K expression in like populations of cells (e.g., two pools of cells that endogenously or recombinantly express EEF2K) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that EEF2K mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the EEF2K protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve EEF2K mRNA expression, may also be used to test nucleic acid modulators.

Secondary Assays

Secondary assays may be used to further assess the activity of EEF2K-modulating agent identified by any of the above methods to confirm that the modulating agent affects EEF2K in a manner relevant to the PTEN/AKT pathway. As used herein, EEF2K-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with EEF2K.

Secondary assays generally compare like populations of cells or animals (e.g., two pools of cells or animals that endogenously or recombinantly express EEF2K) in the presence and absence of the candidate modulator. In general, such assays test whether treatment of cells or animals with a candidate EEF2K-modulating agent results in changes in the PTEN/AKT pathway in comparison to untreated (or mock- or placebo-treated) cells or animals. Certain assays use "sensitized genetic backgrounds", which, as used herein, describe cells or animals engineered for altered expression of genes in the PTEN/AKT or interacting pathways.

Cell-Based Assays

Cell based assays may detect endogenous PTEN/AKT pathway activity or may rely on recombinant expression of PTEN/AKT pathway components. Any of the aforementioned assays may be used in this cell-based format. Candidate modulators are typically added to the cell media but may also be injected into cells or delivered by any other efficacious means.

Animal Assays

A variety of non-human animal models of normal or defective PTEN/AKT pathway may be used to test candidate EEF2K modulators. Models for defective PTEN/AKT pathway typically use genetically modified animals that have been engineered to mis-express (e.g., over-express or lack expression in) genes involved in the PTEN/AKT pathway. Assays generally require systemic delivery of the candidate modulators, such as by oral administration, injection, etc.

In a preferred embodiment, PTEN/AKT pathway activity is assessed by monitoring neovascularization and angiogenesis. Animal models with defective and normal PTEN/AKT are used to test the candidate modulator's affect on EEF2K in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the EEF2K. The mixture is then injected subcutaneously(SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on EEF2K is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the EEF2K endogenously are injected in the flank, $1 \times 10^5$ to $1 \times 10^7$ cells per mouse in a volume of 100 µL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812). An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific EEF2K-modulating agents are useful in a variety of diagnostic and therapeutic applications where disease or disease prognosis is related to defects in the PTEN/AKT pathway, such as angiogenic, apoptotic, or cell proliferation disorders. Accordingly, the invention also provides methods for modulating the PTEN/AKT pathway in a cell, preferably a cell pre-determined to have defective or impaired PTEN or AKT function (e.g. due to overexpression, underexpression, or misexpression of PTEN or AKT, or due to gene mutations), comprising the step of administering an agent to the cell that specifically modulates EEF2K activity. Preferably, the modulating agent produces a detectable phenotypic change in the cell indicating that the PTEN/AKT function is restored. The phrase "function is restored", and equivalents, as used herein, means that the desired phenotype is achieved, or is brought closer to normal compared to untreated cells. For example, with restored PTEN/AKT function, cell proliferation and/or progression through cell cycle may normalize, or be brought closer to normal relative to untreated cells. The invention also provides methods for treating disorders or disease associated with impaired PTEN/AKT function by administering a therapeutically effective amount of an EEF2K-modulating agent that modulates the PTEN/AKT pathway. The invention further provides methods for modulating EEF2K function in a cell, preferably a cell pre-determined to have defective or impaired EEF2K function, by administering an EEF2K-modulating agent. Additionally, the invention provides a method for treating disorders or disease associated with impaired EEF2K function by administering a therapeutically effective amount of an EEF2K-modulating agent.

The discovery that EEF2K is implicated in PTEN/AKT pathway provides for a variety of methods that can be employed for the diagnostic and prognostic evaluation of diseases and disorders involving defects in the PTEN/AKT pathway and for the identification of subjects having a predisposition to such diseases and disorders.

Various expression analysis methods can be used to diagnose whether EEF2K expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective PTEN/AKT signaling that express an EEF2K, are identified as amenable to treatment with an EEF2K modulating agent. In a preferred application, the PTEN/AKT defective tissue overexpresses an EEF2K relative to normal tissue. For example, a Northern blot analysis of mRNA from tumor and normal cell lines, or from tumor and matching normal tissue samples from the same patient, using full or partial EEF2K cDNA sequences as probes, can determine whether particular tumors express or overexpress EEF2K. Alternatively, the TaqMan® is used for quantitative RT-PCR analysis of EEF2K expression in cell lines, normal tissues and tumor samples (PE Applied Biosystems).

Various other diagnostic methods may be performed, for example, utilizing reagents such as the EEF2K oligonucleotides, and antibodies directed against an EEF2K, as described above for: (1) the detection of the presence of EEF2K gene mutations, or the detection of either over- or under-expression of EEF2K mRNA relative to the non-disorder state; (2) the detection of either an over- or an under-abundance of EEF2K gene product relative to the non-disorder state; and (3) the detection of perturbations or abnormalities in the signal transduction pathway mediated by EEF2K.

Kits for detecting expression of EEF2K in various samples, comprising at least one antibody specific to EEF2K, all reagents and/or devices suitable for the detection of antibodies, the immobilization of antibodies, and the like, and instructions for using such kits in diagnosis or therapy are also provided.

Thus, in a specific embodiment, the invention is drawn to a method for diagnosing a disease or disorder in a patient that is associated with alterations in EEF2K expression, the method comprising: a) obtaining a biological sample from the patient; b) contacting the sample with a probe for EEF2K expression; c) comparing results from step (b) with a control; and d) determining whether step (c) indicates a likelihood of the disease or disorder. Preferably, the disease is cancer. The probe may be either DNA or protein, including an antibody.

EXAMPLES

The following experimental section and examples are offered by way of illustration and not by way of limitation.

I. PTEN/AKT Screen

We designed a genetic screen to identify suppressors genes that when inactivated, decrease signaling through the PTEN/AKT pathway. Small interfering RNA (siRNA) libraries targeting genes from the human genome were used for these experiments. The function of individual genes was inactivated by RNAi using siRNAs designed against each gene and transfected into the human lung tumor cell line A549. The siRNA treated cells were assayed for PTEN/AKT pathway activity by monitoring changes in the amount of phosphorylated PRAS40 protein in the cytoplasm of cells (a direct AKT substrate, indicating changes in AKT activity) or the amount of phosphorylated RPS6 protein in the cytoplasm (a direct substrate of the p70S6 Kinase which is a substrate of TOR and downstream of AKT.)

Four unique individual siRNA duplexes per gene were used to knock down expression of each target. Each siRNA duplex was transfected at a final concentration of 25 nM using OligofectAmine™ lipid reagent following manufacturers' instructions (Invitrogen). A gene was scored as positive if two or more individual siRNAs reduced the amount of phosphorylated PRAS40 or RPS6 protein in A549 cells compared to negative control siRNAs. The positive result was repeated in A549 cells and a second cell line, MDA-MB-231T breast cancer cells. The reduction in phospho protein was detected and quantitated on the Cellomics® Arrayscan fluorescent microscopy platform 72 hours post transfection. The screen resulted in identification of genes that when inactivated decrease signaling through the PTEN/AKT pathway. See Table 2 for a listing of siRNAs that specifically knocked down expression of the EEF2K gene in various assays.

II. Analysis of Table 1

The columns "MPTENAKT symbol", and "MPTENAKT name aliases" provide a symbol and the known name abbreviations for the Targets, where available, from Genbank. "MPTENAKT RefSeq_NA or GI_NA", "MPTENAKT GI_AA", "MPTENAKT NAME", and "MPTENAKT Description" provide the reference DNA sequences for the MPTENAKT as available from National Center for Biology Information (NCBI), MPTENAKT protein Genbank identifier number (GI#), MPTENAKT name, and MPTENAKT description, all available from Genbank, respectively. The length of each amino acid is in the "MPTENAKT Protein Length" column.

TABLE 1

| MPTENAKT symbol | MPTENAKT name aliases | MPTENAKT RefSeq_NA or GI_NA | MPTENAKT GI_AA | MPTENAKT name | MPTENAKT description | MPTENAKT protein length |
|---|---|---|---|---|---|---|
| FLJ23119 | leucine-rich repeat kinase 1\|KIAA1790\|hypothetical protein FLJ23119\|FLJ23119\|LRRK1 | 33469142 | 33469143 | na | na | 1310 |
| BAI1 | brain-specific angiogenesis inhibitor 1\|BAI1 | NM_001702 | 4502355 | brain-specific angiogenesis inhibitor 1 | cell adhesion molecule; protein binding; brain-specific angiogenesis inhibitor | 1584 |
| FZD1 | frizzled (*Drosophila*) homolog 1\|FZD1\|Wnt receptor\|Frizzled, *drosophila*, homolog of, 1\|frizzled homolog 1 (*Drosophila*)\|frizzled, *Drosophila*, homolog of, 1\|frizzled-1\|Fz-1\|Fz1\|frizzled 1 | NM_003505 | 4503825 | frizzled homolog 1 (*Drosophila*) | receptor; transmembrane receptor | 647 |
| CCR6 | CC chemokine receptor 6\|chemokine (C-C motif) receptor 6\|seven-transmembrane | NM_004367\|NM_031409 | 4757940 | chemokine (C-C motif) receptor 6 | receptor binding; chemokine receptor; receptor; C-C chemokine receptor; C-C | 374 |

TABLE 1-continued

| MPTENAKT symbol | MPTENAKT name aliases | MPTENAKT RefSeq_NA or GI_NA | MPTENAKT GI_AA | MPTENAKT name | MPTENAKT description | MPTENAKT protein length |
|---|---|---|---|---|---|---|
| | receptor, lymphocyte, 22\|G protein-coupled receptor 29\|chemokine (C-C) receptor 6\|chemokine receptor-like 3\|GPR-CY4\|STRL22\|GPRCY4\|CMKBR6\|CKR-L3\|GPR29\|DRY-6\|CKRL3\|DCR2\|CKR6\|BN-1\|CCR6 | | | | chemokine receptor; G-protein coupled receptor | |
| ACVRL1 | ACVRL1\|activin A receptor type II-like 1\|Activin A receptor, type II-like kinase 1\|ACVRLK1\|ALK-1\|SKR3\|ORW2\|HHT2\|ALK1\|HHT | NM_000020 | 4557243 | activin A receptor type II-like 1 | protein binding; transmembrane receptor protein serine/threonine kinase | 503 |
| NEK8 | NIMA (never in mitosis gene a)-related kinase 8\|NIMA-related kinase 12a\|NEK12A\|NEK8\|ENSP292086 | NM_178170 | 30039692 | NIMA (never in mitosis gene a)-related kinase 8 | na | 692 |
| COASY | COASY\|Coenzyme A synthase\|PPAT\|UKR1\|CoASY\|pOV-2\|coenzyme A synthase\|phosphopantetheine adenylyltransferase/dephosphocoenzyme A kinase\|nucleotide binding protein\|NBP\|bifunctional phosphopantetheine adenylyltransferase/dephospho CoA kinase (PPAT) mRNA\|bifunctional phosphopantetheine adenylyltransferase/dephospho CoA kinase\|DPCK | NM_025233 | 46048207 | Coenzyme A synthase | nucleotidyltransferase | 564 |
| TPK1 | thiamin pyrophosphokinase 1\|mouse thiamin pyrophosphokinase homolog\|thiamine pyrophosphokinase\|HTPK1\|TPK1 | NM_022445 | 21362110 | thiamin pyrophosphokinase 1 | thiamin pyrophosphokinase | 243 |
| GPRC5D | G protein-coupled receptor, family C, group 5, member D\|orphan G-protein coupled receptor\|GPRC5D | NM_018654 | 8923705 | G protein-coupled receptor, family C, group 5, member D | metabotropic glutamate, GABA-B-like receptor; G-protein coupled receptor, unknown ligand | 345 |
| STK35 | CLP-36 interacting kinase\|CLIK1\|bA550O8.2\|Clik1\|STK35\|serine/threonine kinase 35\|bA550O8.2\|CLIK1 | NM_080836 | 18592261 | serine/threonine kinase 35 | protein kinase; protein serine/threonine kinase; ATP binding | 401 |
| ALDH18A1 | ALDH18A1\|aldehyde dehydrogenase 18 family, member A1\|GSAS\|P5CS\|Pyrroline-5-carboxylate | NM_002860 | 21361368 | aldehyde dehydrogenase 18 family, member A1 | glutamate-5-semialdehyde dehydrogenase; glutamate 5-kinase; N-acetyl- | 795 |

TABLE 1-continued

| MPTENAKT symbol | MPTENAKT name aliases | MPTENAKT RefSeq_NA or GI_NA | MPTENAKT GI_AA | MPTENAKT name | MPTENAKT description | MPTENAKT protein length |
|---|---|---|---|---|---|---|
| | synthetase\|pyrroline-5-carboxylate synthetase (glutamate gamma-semialdehyde synthetase)\|PYCS | | | | gamma-glutamyl-phosphate reductase | |
| EMR2 | egf-like module containing, mucin-like, hormone receptor-like 2\|egf-like module containing, mucin-like, hormone receptor-like sequence 2\|EMR2 | NM_013447\| NM_152916\| NM_152917\| NM_152918\| NM_152919\| NM_152920\| NM_152921 | 23397681 | egf-like module containing, mucin-like, hormone receptor-like 2 | protein binding; G-protein coupled receptor | 823 |
| LMTK3 | LMTK3\|lemur tyrosine kinase 3\|TYKLM3\|KIAA1883 protein\|KIAA1883\|LMR3 | XM_055866 | 51474757 | lemur tyrosine kinase 3 | protein kinase; ATP binding; transmembrane receptor protein tyrosine kinase | 1623 |
| AK3 | mitochondrial adenylate kinase isoenzyme 4\|nucleoside-triphosphate-adenylate kinase\|mitochondrial adenylate kinase-3\|ATP-AMP transphosphorylase\|adenylate kinase isozyme 3\|AK-3\|adenylate kinase-3\|AK3\|adenylate kinase 3\|Adenylate kinase-3, mitochondrial\|GTP:AMP phosphotransferase\|AK4\|adenylate kinase-3, mitochondrial\|adenylate kinase isoenzyme 4, mitochondrial | NM_001005353\| NM_013410\| NM_203464 | 8051579 | adenylate kinase 3 | adenylate kinase | 223 |
| EPHB6 | EPH receptor B6\|HEP\|ephrin receptor EphB6\|EphB6\|EPHB6 | NM_004445 | 4758292 | EPH receptor B6 | receptor; protein kinase binding; ephrin receptor | 1006 |
| CCRK | p42\|cell cycle related kinase\|CCRK\|CDCH\|cyclin-dependent protein kinase H | NM_012119\| NM_178432 | 7106269 | cell cycle related kinase | protein kinase; protein serine/threonine kinase; ATP binding | 452 |
| EEF2K | eukaryotic elongation factor-2 kinase\|EEF-2K\|HSU93850\|calmodulin-dependent protein kinase III\|elongation factor-2 kinase\|EEF2K\|eEF-2K\|MGC45041\|eEF-2 kinase\|calcium/calmodulin-dependent eukaryotic elongation factor-2 kinase\|eEF2K | NM_013302 | 9558749 | eukaryotic elongation factor-2 kinase | calcium/calmodulin-dependent protein kinase; protein serine/threonine kinase; ATP binding; translation factor, nucleic acid binding; eukaryotic translation initiation factor 2alpha kinase | 725 |
| STK17B | STK17B\|serine/threonine kinase 17b (apoptosis-inducing)\|death-associated protein kinase-related 2\|DRAK2 | NM_004226 | 4758194 | serine/threonine kinase 17b (apoptosis-inducing) | protein serine/threonine kinase | 372 |

TABLE 1-continued

| MPTENAKT symbol | MPTENAKT name aliases | MPTENAKT RefSeq_NA or GI_NA | MPTENAKT GI_AA | MPTENAKT name | MPTENAKT description | MPTENAKT protein length |
|---|---|---|---|---|---|---|
| STYK1 | NOK\|DKFZp761P1010\|SuRTK106\|hypothetical protein DKFZp761P1010\|DKFZP761P1010\|STYK1\|protein kinase STYK1 | NM_018423 | 8922179 | protein kinase STYK1 | protein kinase; ATP binding; transmembrane receptor protein tyrosine kinase; protein tyrosine kinase | 495 |
| LTB4R2 | leukotriene B4 receptor-2\|leukotriene B(4) receptor 2\|leukotriene B4 receptor 2\|seven transmembrane receptor BLTR2\|leukotriene B4 receptor BLT2\|JULF2\|BLTR2\|BLT2\|LTB4R2 | NM_019839 | 9789897 | leukotriene B4 receptor 2 | leukotriene receptor | 389 |
| PRKCE | nPKC-epsilon\|PKCE\|protein kinase C, epsilon\|PRKCE\|PKCe | NM_005400 | 4885563 | protein kinase C, epsilon | protein kinase; protein binding; calcium independent protein kinase C; diacylglycerol-activated/phospholipid dependent protein kinase C; signal transducer; protein kinase C | 737 |
| CCR9 | G protein-coupled receptor 28\|GPR28\|CCR9\|GPR-9-6\|chemokine (C-C motif) receptor 9\|CC chemokine receptor 9 | NM_006641\|NM_031200 | 14043042 | chemokine (C-C motif) receptor 9 | chemokine receptor; chemokine receptor; chemokine receptor; superoxide-generating NADPH oxidase activator; C-C chemokine receptor; C-C chemokine receptor; G-protein coupled receptor | 369 |
| KIAA1811 | SAD1 kinase\|KIAA1811 protein\|KIAA1811\|BRSK1 | NM_032430 | 24308326 | KIAA1811 protein | protein kinase; protein serine/threonine kinase; protein serine/threonine kinase; ATP binding | 715 |
| PNKP | polynucleotide kinase 3'-phosphatase\|polynucleotide kinase 3-prime-phosphatase\|PNK\|PNKP | NM_007254 | 31543419 | polynucleotide kinase 3'-phosphatase | kinase; phosphatase | 521 |
| APEG1 | striated muscle preferentially expressed protein\|KIAA1297 protein\|KIAA1297\|SPEG\|MGC12676\|nuclear protein, marker for differentiated aortic smooth muscle and down-regulated with vascular injury\|aortic preferentially expressed protein 1\|APEG1 | NM_005876\|XM_051005 | 7242949 | aortic preferentially expressed protein 1 | na | 2242 |

TABLE 1-continued

| MPTENAKT symbol | MPTENAKT name aliases | MPTENAKT RefSeq_NA or GI_NA | MPTENAKT GI_AA | MPTENAKT name | MPTENAKT description | MPTENAKT protein length |
|---|---|---|---|---|---|---|
| BLR1 | BCA-1 receptor\|Burkitt lymphoma receptor 1, GTP binding protein (chemokine (C-X-C motif) receptor 5)\|Burkitt lymphoma receptor 1, GTP-binding protein\|Burkitt lymphoma receptor 1, GTP binding protein\|C-X-C chemokine receptor type 5\|monocyte-derived receptor 15\|MDR15\|CXCR5\|BLR1 | NM_001716\| NM_032966 | 4502415 | Burkitt lymphoma receptor 1, GTP binding protein (chemokine (C-X-C motif) receptor 5) | chemokine receptor; C-X-C chemokine receptor; superoxide-generating NADPH oxidase activator; G-protein coupled receptor | 372 |
| TAF1L | TAF1-like RNA polymerase II, TATA box binding protein (TBP)-associated factor, 210 kD\|TAF1L\|TAF2A2\|TBP-associated factor RNA polymerase 1-like\|TAF1-like RNA polymerase II, TATA box binding protein (TBP)-associated factor, 210 kDa | NM_153809 | 24429572 | TAF1-like RNA polymerase II, TATA box binding protein (TBP)-associated factor, 210 kDa | protein binding; general RNA polymerase II transcription factor | 1826 |
| C9orf12 | chromosome 9 open reading frame 12\|1,3,4,5,6-pentakisphosphate 2-kinase\|FLJ13163\|INSP5K2\|C9orf12 | NM_022755 | 12232423 | chromosome 9 open reading frame 12 | na | 491 |
| PAK6 | p21(CDKN1A)-activated kinase 6\|p21-activated protein kinase 6\|PAK5\|PAK6 | NM_020168 | 9910476 | p21(CDKN1A)-activated kinase 6 | protein kinase; kinase; protein serine/threonine kinase; ATP binding; transcription co-repressor; receptor-associated protein | 681 |

TABLE 2 siRNAs used to knockdown expression of the EEF2K gene in various assays.

| siRNA sequences | SEQ ID NOs |
|---|---|
| CGAAGAAGCUCUCCAACUU | SEQ ID NO: 6 |
| GGAUGGCUCUCUUCUUCUA | SEQ ID NO: 7 |
| GAACAUGGCCACUCAUACA | SEQ ID NO: 8 |
| GCAGUUGCCUCAUCACAUC | SEQ ID NO: 9 |

III. High-Throughput In Vitro Fluorescence Polarization Assay

Fluorescently-labeled EEF2K peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of EEF2K activity.

IV. High-Throughput In Vitro Binding Assay.

$^{33}$P-labeled EEF2K peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate PTEN/AKT modulating agents.

V. Immunoprecipitations and Immunoblotting

For coprecipitation of transfected proteins, $3 \times 10^6$ appropriate recombinant cells containing the EEF2K proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

VI. Kinase Assay

A purified or partially purified EEF2K is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VII. Expression Analysis

All cell lines used in the following experiments are NCI (National Cancer Institute) lines, and are available from ATCC (American Type Culture Collection, Manassas, Va. 20110-2209). Normal and tumor tissues are obtained from Impath, UC Davis, Clontech, Stratagene, Ardais, Genome Collaborative, and Ambion.

TaqMan® analysis is used to assess expression levels of the disclosed genes in various samples.

RNA is extracted from each tissue sample using Qiagen (Valencia, Calif.) RNeasy kits, following manufacturer's protocols, to a final concentration of 50 ng/µl. Single stranded cDNA is then synthesized by reverse transcribing the RNA samples using random hexamers and 500 ng of total RNA per reaction, following protocol 4304965 of Applied Biosystems (Foster City, Calif.).

Primers for expression analysis using TaqMan® assay (Applied Biosystems, Foster City, Calif.) are prepared according to the TaqMan® protocols, and the following criteria: a) primer pairs are designed to span introns to eliminate genomic contamination, and b) each primer pair produced only one product. Expression analysis is performed using a 7900HT instrument.

TaqMan® reactions are carried out following manufacturer's protocols, in 25 µl total volume for 96-well plates and 10 µl total volume for 384-well plates, using 300 nM primer and 250 nM probe, and approximately 25 ng of cDNA. The standard curve for result analysis is prepared using a universal pool of human cDNA samples, which is a mixture of cDNAs from a wide variety of tissues so that the chance that a target will be present in appreciable amounts is good. The raw data are normalized using 18S rRNA (universally expressed in all tissues and cells).

For each expression analysis, tumor tissue samples are compared with matched normal tissues from the same patient. A gene is considered overexpressed in a tumor when the level of expression of the gene is 2 fold or higher in the tumor compared with its matched normal sample. In cases where normal tissue is not available, a universal pool of cDNA samples is used instead. In these cases, a gene is considered overexpressed in a tumor sample when the difference of expression levels between a tumor sample and the average of all normal samples from the same tissue type is greater than 2 times the standard deviation of all normal samples (i.e., Tumor−average(all normal samples)>2×STDEV(all normal samples)).

The EEF2K gene is expressed at slightly lower levels in breast cancer tumors, including basal cell tumors and luminal tumors, ovarian tumors, and prostate tumors relative to non-tumor tissue. The EEF2K gene is expressed at significantly lower levels in colon tumors, and lung tumors. The EEF2K gene is overexpressed in kidney, liver and pancreatic tumors (p-values 0.0001, 0.0006, 0.0003 respectively) relative to normal tissues. The EEF2K gene is significantly underexpressed in uterine tumors (p-value 0.0014) relative to normal uterine tissue.

The EEF2K gene is highly expressed in a number of cell lines including the MDA_Mb_435, and MCF7 breast cell lines. The EEF2K gene is highly expressed in the HCT_116, HCT_116_TX15CR, HCT_116_VP35, HCT_116_EPO5, HCT_116_vivo, DLD_1, LS174T, and HCT_116_ras colon cell lines. The EEF2K gene is highly expressed in EK293 kidney cell line. The EEF2K gene is highly expressed in U937, HL_60_TB and K_562 leukemia cell lines. The EEF2K gene is highly expressed in CALU_6, LX_1 and A549 lung cell lines. The EEF2K gene is highly expressed in the HT_1080 muscle, SK_OV_3 ovary, OVCAR_3 ovary, PANC_1 pancreas and LNCaP prostate cell lines.

A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

VIII. Cellular Assays

We performed cellular assays in mammalian cells to validate targets that were identified in a genetic screen as suppressor genes that when inactivated, decrease signaling through the AKT pathway. (see Hsieh A C et al. (2004) NAR 32(3):893-901. as a proof of principle for an siRNA screen for PTEN pathway modifiers.) The function of individual genes was inactivated by RNAi using siRNAs designed against each gene and transfected into the human tumor cell lines A549, MDA-MB231-T, and PC-3 cells. The siRNA treated cells were assayed for AKT pathway activity by monitoring changes in three relevant pathway readouts: 1) The amount of phosphorylated PRAS40 protein in the cytoplasm of cells (a direct AKT substrate, indicating changes in AKT activity); 2) the amount of phosphorylated RPS6 protein in the cytoplasm (a direct substrate of the p70S6 Kinase which is a substrate of TOR and downstream of AKT.); and 3) The amount of phosphorylation of Akt substrates as a whole by the use of an antibody which recognizes the consensus phosphorylation site in these substrates.

4 unique individual siRNA duplexes per gene were used to knock down expression of each target. Each siRNA duplex was transfected at a final concentration of 25 nM using OligofectAmine lipid reagent following manufacturer's instructions (Invitrogen). A gene was scored as positive if two or more individual siRNAs reduced the amount of phosphorylated PRAS40 or RPS6 protein or Akt substrate phosphorylation in the cell types described above compared to negative control siRNAs. The reduction in phospho protein was detected and quantified on the Cellomics Arrayscan fluorescent microscopy platform 72 hours post transfection. Positive results in these validation assays confirm that these targets, when inactivated, decrease signaling through the AKT pathway. The siRNAs identified in Table 2 reduced the amount of Phospho-RPS6 greater than 40% in A549 cells and in varying amounts in MB231T cells and PC3 cells. The siRNAs were in Table 2 were able to reduce the amount of Pras40 by 20-30% in PC3 cells and the phosphorylation of AKT substrate by 40-60% in A549 cells, MB231T cells and PC3 cells.

In addition, these targets were validated in several cell based assays designed to look at the effect of target knockdown on phenotypic endpoints such as reduction of proliferation and induction of apoptosis.

Apoptosis Assays.

Apoptosis or programmed cell death is a suicide program is activated within the cell, leading to fragmentation of DNA, shrinkage of the cytoplasm, membrane changes and cell death. Apoptosis is mediated by proteolytic enzymes of the caspase family. Many of the altering parameters of a cell are measurable during apoptosis.

Caspase 3 Assay:

The caspase 3 assay is based on the activation of the caspase cleavage activity as part of a cascade of events that occur during programmed cell death in many apoptotic pathways. To determine if mPIENAKT pathway targets induced Caspase 3 mediated apoptosis when target activity is reduced, the cell types A549, PC-3, MDA-MB231-T and U87-MG were treated with 4 unique individual siRNA duplexes per gene to knock down expression of each target. Each siRNA duplex was transfected at a final concentration of 25 nM using OligofectAmine lipid reagent following manufacturer's instructions (Invitrogen). The detection of cleaved caspase 3, indicating an intermediate stage of apoptosis, was detected with an antibody that specifically recognizes this form of caspase 3 and quantified on the Cellomics Arrayscan fluorescent microscopy platform 72 hours post transfection. The siRNAs of Table 2 increased the level of caspase 3 detected in MB231T cells.

Phospho Histone H2B Assay:

The Phospho-histone H2B assay is another apoptosis assay, based on phosphorylation of histone H2B as a result of apoptosis. A fluorescent dye that is associated with phosphohistone H2B is used to measure the increase of phosphohistone H2B as a result of apoptosis. To determine if mPTENAKT pathway targets induce phosphohistone H2B mediated apoptosis when target activity is reduced, the cell types A549, PC-3, MDA-MB231-T and U87-MG were treated with 4 unique individual siRNA duplexes per gene to knock down expression of each target. Each siRNA duplex was transfected at a final concentration of 25 nM using OligofectAmine lipid reagent following manufacturer's instructions (Invitrogen). The detection of phospho histone H2B, indicating induction of apoptosis, was detected with an antibody that specifically recognizes phosphorylated histone H2B and quantified on the Cellomics Arrayscan fluorescent microscopy platform 72 hours post transfection. The EEF2K siRNAs of Table 2 induced the phosphorylation of histone H2B in 231T cells and in PC3 cells.

Cell Proliferation and Cell Count Assays.

To determine if the PTEN pathway targets reduce cell proliferation a bromodeoxyuridine (BRDU) incorporation assay was performed. This assay identifies a cell population undergoing DNA synthesis by incorporation of BRDU into newly-synthesized DNA. Newly-synthesized DNA is then detected using an anti-BRDU antibody (Hoshino et al., 1986, Int. J. Cancer 38, 369; Campana et al., 1988, J. Immunol. Meth. 107, 79). To determine if mPTENAKT pathway targets reduce BrdU incorporation and therefore cellular proliferation when target activity is reduced, the cell types A549, PC-3, MDA-MB231-T and U87-MG were treated with 4 unique individual siRNA duplexes per gene to knock down expression of each target. Each siRNA duplex was transfected at a final concentration of 25 nM using OligofectAmine lipid reagent following manufacturer's instructions (Invitrogen). At 72 hours post-transfection, BrdU was added to the cells for 4 hours to allow incorporation. To measure whether BrdU and therefore proliferation was reduced following target inactivation, BrdU was detected with an anti-BrdU antibody and quantified on the Cellomics Arrayscan fluorescent microscopy platform. The EEF2K siRNAs of Table 2 decreased BrdU incorporation in 231T cells, A549 cells, PC3 cells and U87MG cells 40-60%.

In addition, to measure if target inactivation results in reduction in cell number, the cell types A549, PC-3, MDA-MB231-T and U87-MG were treated with 4 unique individual siRNA duplexes per gene to knock down expression of each target. Each siRNA duplex was transfected at a final concentration of 25 nM using OligofectAmine lipid reagent following manufacturer's instructions (Invitrogen). At 72 hours, the Hoescht reagent was added, which incorporates into chromosomal DNA and serves to demarcate the nucleus of each individual cell. Incorporation of Hoescht was then quantified on the Cellomics Arrayscan fluorescent microscopy platform. The siRNAs of Table 2 reduced the cell counts in A549 cells, MB231T cells, PC3 cells and U87MG cells.

What is claimed is:

1. A method of identifying a candidate PTEN/AKT pathway modulating agent, said method comprising the steps of:
   (a) providing an in vitro cell system comprising a Eukaryotic Elongation Factor 2 Kinase (EEF2K) polypeptide comprising SEQ ID NO: 1;
   (b) contacting the assay system with a test agent that modulates the expression or activity of the EEF2K polypeptide, wherein the test agent is selected from a chemically-synthesized organic small molecule having a molecular weight less than 5000D, an EEF2K-interacting protein, and an EEF2K-specific antibody; and
   (c) identifying the test agent as a candidate PTEN/AKT pathway modulating agent by determining a change in the activity of the assay system in the presence of the test agent of step (b) compared with the absence of the test agent.

2. The method of claim 1 wherein the assay system comprises cultured cells that express the EEF2K polypeptide.

3. The method of claim 2 wherein the cultured cells additionally have defective PTEN/AKT function.

4. The method of claim 1 wherein the assay system is a binding assay.

5. The method of claim 1 wherein the assay system is selected from the group consisting of an apoptosis assay system, a cell proliferation assay system, an angiogenesis assay system, and a hypoxic induction assay system.

6. The method of claim 1 wherein test agent is an EEF2K specific antibody.

7. The method of claim 1, comprising the additional steps of:
- (d) providing a second assay system capable of detecting a change in the activity of the PTEN/AKT pathway comprising cultured cells expressing the EEF2K polypeptide,
- (e) contacting the second assay system with the test agent of step (b); and
- (f) confirming the test agent as a candidate PTEN/AKT pathway modulating agent by determining a change in the activity of the PTEN/AKT pathway in the presence of the test agent compared with the absence of the test agent.

* * * * *